US012788387B2

(12) United States Patent
Heo et al.

(10) Patent No.: US 12,788,387 B2
(45) Date of Patent: Nov. 10, 2026

(54) SPINAL IMPLANT DELIVERY DEVICE FOR PROTECTING TISSUE

(71) Applicant: Amplify Surgical, Inc., Irvine, CA (US)

(72) Inventors: Dong-Hwa Heo, Seoul (KR); Andy Wonyong Choi, Irvine, CA (US)

(73) Assignee: Amplify Surgical, Inc., Foothill Ranch, CA (US)

( * ) Notice: Subject to any disclaimer, the term of this patent is extended or adjusted under 35 U.S.C. 154(b) by 20 days.

(21) Appl. No.: 18/987,830

(22) Filed: Dec. 19, 2024

(65) Prior Publication Data

US 2025/0195113 A1 Jun. 19, 2025

Related U.S. Application Data

(60) Provisional application No. 63/611,913, filed on Dec. 19, 2023.

(51) Int. Cl.
*A61B 17/02* (2006.01)
*A61B 17/56* (2006.01)
(Continued)

(52) U.S. Cl.
CPC ............ *A61B 17/025* (2013.01); *A61B 90/03* (2016.02); *A61B 90/08* (2016.02); *A61B 90/361* (2016.02);
(Continued)

(58) Field of Classification Search
CPC ........... A61F 2/4611; A61F 2002/4627; A61B 17/3439; A61B 2017/0256
See application file for complete search history.

(56) References Cited

U.S. PATENT DOCUMENTS 619,413 A 2/1899 Higgins
3,486,505 A 12/1969 Morrison
(Continued)

FOREIGN PATENT DOCUMENTS

AU 2013206287 7/2013
AU 2013262504 1/2015
(Continued)

OTHER PUBLICATIONS

U.S. Appl. No. 18/335,737, filed Jun. 15, 2023, Anchored Intervertebral Implants.
(Continued)

*Primary Examiner* — Jacqueline T Johanas
(74) *Attorney, Agent, or Firm* — Ashurst Perkins Coie US LLP

(57) ABSTRACT

A spinal implant delivery device can include a pair of insertion members that can be inserted into a subject towards, for example, an intervertebral space or other target site for a spinal implant. The insertion members can define a channel with an open side and a slot through which an instrument or implant cannot exit the channel. The slot thereby protects adjacent tissue and nerves from potential damage during a surgical procedure. The insertion members can include distance indicators and/or a plurality of apertures. The distance indicators can be used to visually determine how deep the insertion members are inserted into a subject at any given time. The apertures can provide a direct view into the channel of the spinal implant delivery device, allowing a surgeon or other user to visually determine the position of an instrument or implant disposed in the channel.

32 Claims, 12 Drawing Sheets

(51) Int. Cl.
*A61B 90/00* (2016.01)
*A61F 2/46* (2006.01)
*A61B 17/00* (2006.01)

(52) U.S. Cl.
CPC ... *A61F 2/4611* (2013.01); *A61B 2017/00367* (2013.01); *A61B 2017/00902* (2013.01); *A61B 2017/0256* (2013.01); *A61B 2017/564* (2013.01); *A61B 2090/036* (2016.02); *A61B 2090/0807* (2016.02)

(56) References Cited

U.S. PATENT DOCUMENTS

| | | | | |
|---|---|---|---|---|
| 4,164,225 | A | 8/1979 | Johnson | |
| 4,456,005 | A | 6/1984 | Lichty | |
| 4,657,550 | A | 4/1987 | Daher | |
| 4,834,757 | A | 5/1989 | Brantigan | |
| 4,858,601 | A | 8/1989 | Glisson | |
| 4,863,476 | A | 9/1989 | Shepperd | |
| 5,059,193 | A | 10/1991 | Kuslich | |
| 5,171,278 | A | 12/1992 | Pisharodi | |
| 5,171,279 | A | 12/1992 | Mathews | |
| 5,290,312 | A | 3/1994 | Kojimoto | |
| 5,306,310 | A | 4/1994 | Siebels | |
| 5,336,223 | A | 8/1994 | Rogers | |
| 5,390,683 | A | 2/1995 | Pisharodi | |
| 5,405,391 | A | 4/1995 | Hednerson | |
| 5,425,772 | A | 6/1995 | Brantigan | |
| 5,437,637 | A | 8/1995 | Lieber et al. | |
| 5,443,514 | A | 8/1995 | Steffee | |
| 5,458,641 | A | 10/1995 | Ramirez | |
| 5,554,191 | A | 9/1996 | Lahille | |
| 5,571,192 | A | 11/1996 | Schonhoffer | |
| 5,609,635 | A | 3/1997 | Michelson | |
| 5,653,762 | A | 8/1997 | Pisharodi | |
| 5,653,763 | A | 8/1997 | Errico | |
| 5,658,335 | A | 8/1997 | Allen | |
| 5,665,122 | A | 9/1997 | Kambin | |
| 5,690,222 | A | 11/1997 | Peters | |
| 5,693,100 | A | 12/1997 | Pisharodi | |
| 5,702,455 | A | 12/1997 | Saggar | |
| 5,716,415 | A | 2/1998 | Steffee | |
| 5,735,290 | A | 4/1998 | Sterman et al. | |
| 5,762,629 | A | 6/1998 | Kambin | |
| 5,776,198 | A | 7/1998 | Rabbe | |
| 5,782,832 | A | 7/1998 | Larsen et al. | |
| 5,846,182 | A | 12/1998 | Wolcott | |
| 5,865,848 | A | 2/1999 | Baker | |
| 5,888,223 | A | 3/1999 | Bray | |
| 5,980,522 | A | 11/1999 | Koros | |
| 5,989,290 | A | 11/1999 | Biedermann | |
| 6,015,436 | A | 1/2000 | Schonhoffer | |
| 6,039,761 | A | 3/2000 | Lim | |
| 6,045,579 | A | 4/2000 | Hochshuler | |
| 6,080,193 | A | 6/2000 | Hochshuler | |
| 6,093,207 | A | 7/2000 | Pisharodi | |
| 6,102,950 | A | 8/2000 | Vaccaro | |
| 6,117,174 | A | 9/2000 | Nolan | |
| 6,126,689 | A | 10/2000 | Brett | |
| 6,126,869 | A | 10/2000 | Haaland | |
| 6,129,763 | A | 10/2000 | Chauvin | |
| 6,159,244 | A | 12/2000 | Suddaby | |
| 6,162,170 | A | 12/2000 | Foley et al. | |
| 6,174,334 | B1 | 1/2001 | Suddaby | |
| 6,176,881 | B1 | 1/2001 | Schumlaut | |
| 6,183,517 | B1 | 2/2001 | Suddaby | |
| 6,190,413 | B1 | 2/2001 | Sutcliffe | |
| 6,190,414 | B1 | 2/2001 | Young | |
| 6,193,756 | B1 | 2/2001 | Studer | |
| 6,193,757 | B1 | 2/2001 | Foley | |
| 6,193,775 | B1 | 2/2001 | Metz | |
| 6,200,348 | B1 | 3/2001 | Biedermann | |
| 6,214,050 | B1 | 4/2001 | Huene | |
| 6,296,647 | B1 | 10/2001 | Robioneck | |
| 6,299,644 | B1 | 10/2001 | Vanderschot | |
| 6,332,895 | B1 | 12/2001 | Suddaby | |
| 6,348,058 | B1 | 2/2002 | Melkent et al. | |
| 6,395,034 | B1 | 5/2002 | Suddaby | |
| 6,409,766 | B1 | 6/2002 | Brett | |
| 6,413,278 | B1 | 7/2002 | Marchosky | |
| 6,419,705 | B1 | 7/2002 | Erickson | |
| 6,436,119 | B1 * | 8/2002 | Erb | A61B 17/3417 606/279 |
| 6,436,140 | B1 | 8/2002 | Liu | |
| 6,454,806 | B1 | 9/2002 | Cohen | |
| 6,491,724 | B1 | 12/2002 | Ferree | |
| 6,517,543 | B1 | 2/2003 | Berrevoets et al. | |
| 6,520,967 | B1 * | 2/2003 | Cauthen | A61B 17/1757 606/86 R |
| 6,562,074 | B2 | 5/2003 | Gerbec | |
| 6,582,431 | B1 | 6/2003 | Ray | |
| 6,641,614 | B1 | 11/2003 | Wagner et al. | |
| 6,648,917 | B2 | 11/2003 | Gerbec | |
| 6,660,038 | B2 | 12/2003 | Boyer | |
| 6,666,891 | B2 | 12/2003 | Boehm | |
| 6,685,742 | B1 | 2/2004 | Jackson | |
| 6,706,070 | B1 | 3/2004 | Wagner | |
| 6,709,458 | B2 | 3/2004 | Michelson | |
| 6,723,126 | B1 | 4/2004 | Berry | |
| 6,730,126 | B2 | 5/2004 | Boehm | |
| 6,746,484 | B1 | 6/2004 | Liu | |
| 6,821,298 | B1 | 11/2004 | Jackson | |
| 6,833,006 | B2 | 12/2004 | Foley | |
| 6,852,129 | B2 | 2/2005 | Gerbec | |
| 6,863,673 | B2 | 3/2005 | Gerbec | |
| 6,893,464 | B2 | 5/2005 | Kiester | |
| 6,921,403 | B2 | 7/2005 | Cragg | |
| 6,969,392 | B2 | 11/2005 | Gitis et al. | |
| 7,070,598 | B2 | 7/2006 | Lim | |
| 7,083,650 | B2 | 8/2006 | Moskowitz et al. | |
| 7,087,055 | B2 | 8/2006 | Lim et al. | |
| 7,112,222 | B2 | 9/2006 | Fraser et al. | |
| 7,217,293 | B2 | 5/2007 | Branch | |
| 7,513,900 | B2 | 4/2009 | Carrison | |
| 7,625,377 | B2 | 12/2009 | Veldhuizen | |
| 7,731,751 | B2 | 6/2010 | Butler et al. | |
| 7,799,057 | B2 | 9/2010 | Hudgins et al. | |
| 7,799,081 | B2 | 9/2010 | McKinley | |
| 7,824,427 | B2 | 11/2010 | Perez-Cruet | |
| 7,846,206 | B2 | 12/2010 | Oglaza | |
| 7,879,098 | B1 | 2/2011 | Simmons | |
| 7,922,729 | B2 | 4/2011 | Michelson | |
| RE42,525 | E | 7/2011 | Simonson | |
| 8,012,207 | B2 | 9/2011 | Kim | |
| 8,016,767 | B2 | 9/2011 | Miles et al. | |
| 8,043,334 | B2 | 10/2011 | Fisher et al. | |
| 8,062,375 | B2 | 11/2011 | Glerum et al. | |
| 8,097,018 | B2 | 1/2012 | Malandain | |
| 8,097,035 | B2 | 1/2012 | Glenn | |
| 8,109,972 | B2 | 2/2012 | Zucherman | |
| 8,110,004 | B2 | 2/2012 | Valdevit | |
| 8,152,837 | B2 | 4/2012 | Atarac | |
| 8,317,798 | B2 | 11/2012 | Lim | |
| 8,323,344 | B2 | 12/2012 | Galley | |
| 8,353,963 | B2 | 1/2013 | Glerum | |
| 8,382,842 | B2 | 2/2013 | Greenhalgh et al. | |
| 8,394,145 | B2 | 3/2013 | Weiman | |
| 8,398,713 | B2 | 3/2013 | Weiman | |
| 8,409,291 | B2 | 4/2013 | Blackwell | |
| 8,425,613 | B2 | 4/2013 | Theofilos | |
| 8,435,298 | B2 | 5/2013 | Weiman | |
| 8,491,657 | B2 | 7/2013 | Attia | |
| 8,491,659 | B2 | 7/2013 | Weiman | |
| 8,496,709 | B2 | 7/2013 | Schell | |
| 8,506,635 | B2 | 8/2013 | Palmatier | |
| 8,512,407 | B2 | 8/2013 | Butler et al. | |
| 8,518,120 | B2 | 8/2013 | Glerum et al. | |
| 8,541,355 | B2 | 9/2013 | Fleckenstein | |
| 8,556,979 | B2 | 10/2013 | Weiman et al. | |
| 8,568,317 | B1 | 10/2013 | Gharib et al. | |
| 8,568,481 | B2 | 10/2013 | Olmos | |
| 8,579,907 | B2 | 11/2013 | Lim | |
| 8,628,576 | B2 | 1/2014 | Triplett | |
| 8,632,594 | B2 | 1/2014 | Williams et al. | |

(56) References Cited

U.S. PATENT DOCUMENTS 8,632,595 B2 1/2014 Weiman
8,652,174 B2 2/2014 Gabelberger
8,663,329 B2 3/2014 Ernst
8,678,576 B2 3/2014 Edombingo
8,679,183 B2 3/2014 Glerum et al.
8,685,095 B2 4/2014 Miller
8,685,098 B2 4/2014 Glerum et al.
8,709,086 B2 4/2014 Glerum
8,777,993 B2 7/2014 Siegal
8,778,027 B2 7/2014 Medina
8,808,385 B1 8/2014 Smith
8,845,731 B2 9/2014 Weiman
8,845,732 B2 9/2014 Weiman
8,845,734 B2 9/2014 Weiman
8,852,279 B2 10/2014 Weiman
8,864,830 B2 * 10/2014 Malandain .............. A61F 2/447 606/86 A
8,864,833 B2 10/2014 Glerum et al.
8,888,853 B2 11/2014 Glerum et al.
8,888,854 B2 11/2014 Glerum et al.
8,900,305 B2 12/2014 Stad
8,926,704 B2 1/2015 Glerum et al.
8,940,048 B2 1/2015 Butler et al.
8,986,386 B2 3/2015 Oglaza et al.
8,986,387 B1 3/2015 To et al.
9,034,041 B2 5/2015 Wolters et al.
9,039,771 B2 5/2015 Glerum et al.
9,044,342 B2 6/2015 Perloff et al.
9,060,876 B1 6/2015 To et al.
9,078,769 B2 7/2015 Farin
9,119,730 B2 9/2015 Glerum et al.
9,125,757 B2 9/2015 Weiman
9,149,367 B2 10/2015 Davenport et al.
9,155,628 B2 10/2015 Glerum et al.
9,186,258 B2 11/2015 Davenport et al.
9,198,765 B1 12/2015 Pimenta
9,198,772 B2 12/2015 Weiman
9,204,972 B2 12/2015 Weiman et al.
9,204,974 B2 12/2015 Glerum et al.
9,211,196 B2 12/2015 Glerum et al.
9,216,095 B2 12/2015 Glerum et al.
9,226,836 B2 1/2016 Glerum
9,271,843 B2 3/2016 Fabian et al.
9,278,008 B2 3/2016 Perloff et al.
9,283,092 B2 3/2016 Siegal et al.
9,295,562 B2 3/2016 Lechmann et al.
9,308,099 B2 4/2016 Triplett et al.
9,320,613 B2 4/2016 Dmuschewsky
9,351,848 B2 5/2016 Glerum et al.
9,358,125 B2 6/2016 Jimenez et al.
9,358,126 B2 6/2016 Glerum et al.
9,358,128 B2 6/2016 Glerum et al.
9,358,129 B2 6/2016 Weiman
9,370,434 B2 6/2016 Weiman
9,402,739 B2 8/2016 Weiman et al.
9,408,708 B2 8/2016 Greenhalgh
9,414,934 B2 8/2016 Cain
9,414,936 B2 8/2016 Miller et al.
9,445,848 B2 9/2016 Anderson et al.
9,445,918 B1 9/2016 Lin
9,452,063 B2 9/2016 Glerum et al.
9,456,903 B2 10/2016 Glerum et al.
9,474,623 B2 10/2016 Cain
9,474,625 B2 10/2016 Weiman
9,480,573 B2 11/2016 Perloff et al.
9,480,578 B2 11/2016 Pinto
9,482,260 B1 11/2016 Krause
9,486,325 B2 11/2016 Davenport et al.
9,486,328 B2 11/2016 Jimenez et al.
9,492,283 B2 11/2016 Glerum
9,492,287 B2 11/2016 Glerum et al.
9,492,288 B2 11/2016 Wagner et al.
9,510,954 B2 12/2016 Glerum et al.
9,522,068 B2 12/2016 Goel et al.
9,539,108 B2 1/2017 Glerum et al.
9,545,319 B2 1/2017 Farin
9,554,918 B2 1/2017 Weiman
9,561,116 B2 2/2017 Weiman et al.
9,561,117 B2 2/2017 Lechmann et al.
9,566,168 B2 2/2017 Glerum et al.
9,579,124 B2 2/2017 Gordon et al.
9,579,130 B2 2/2017 Oglaza et al.
9,585,762 B2 3/2017 Suddaby et al.
9,597,197 B2 3/2017 Lechmann et al.
9,597,200 B2 3/2017 Glerum et al.
9,610,175 B2 4/2017 Barreiro et al.
9,610,176 B1 4/2017 Abdou
9,615,937 B2 4/2017 Barreiro
9,655,744 B1 5/2017 Pimenta
9,820,788 B2 11/2017 Vrionis et al.
9,888,859 B1 2/2018 Spangler et al.
9,901,457 B2 2/2018 Sack et al.
9,937,055 B1 * 4/2018 Bernhardt, Jr. ....... A61F 2/4684
10,105,238 B2 10/2018 Koch et al.
10,143,567 B2 * 12/2018 Costabile ............ A61F 2/30771
10,201,431 B2 2/2019 Slater et al.
10,314,631 B2 6/2019 Blohm et al.
10,322,009 B2 6/2019 Aghayev et al.
10,327,912 B1 6/2019 Suddaby
10,390,963 B2 8/2019 Olmos et al.
10,500,059 B2 12/2019 Grotz
10,687,876 B2 6/2020 Vrionis et al.
10,792,083 B2 10/2020 Vrionis et al.
10,799,367 B2 10/2020 Vrionis et al.
10,898,340 B2 1/2021 Koch et al.
10,945,859 B2 3/2021 Ewer et al.
11,134,997 B2 10/2021 Vrionis et al.
11,246,717 B2 2/2022 Aghayev et al.
11,452,617 B2 * 9/2022 Geist ..................... A61F 2/4611
11,464,648 B2 10/2022 Choi et al.
11,950,770 B1 4/2024 Choi et al.
2001/0005796 A1 6/2001 Zdeblick et al.
2001/0032017 A1 10/2001 Alfaro
2002/0010511 A1 1/2002 Michelson
2002/0107573 A1 8/2002 Steinberg
2002/0143401 A1 10/2002 Michelson
2002/0195827 A1 12/2002 Jackson et al.
2003/0028251 A1 2/2003 Mathews
2003/0060687 A1 3/2003 Kleeman et al.
2003/0208206 A1 11/2003 Gitis et al.
2003/0216748 A1 11/2003 Gitis et al.
2003/0229355 A1 12/2003 Keller
2003/0233145 A1 * 12/2003 Landry ................. A61F 2/4611 606/100
2003/0236472 A1 12/2003 Van Hoeck et al.
2004/0002758 A1 1/2004 Landry
2004/0034430 A1 2/2004 Falahee
2004/0122431 A1 6/2004 Biedermann et al.
2004/0210227 A1 10/2004 Trail et al.
2005/0043735 A1 2/2005 Ahmad
2005/0070911 A1 3/2005 Carrison et al.
2005/0113917 A1 5/2005 Chae et al.
2005/0143735 A1 6/2005 Kyle et al.
2005/0177235 A1 8/2005 Bahnham
2005/0182416 A1 8/2005 Lim
2005/0197660 A1 9/2005 Haid et al.
2005/0222681 A1 10/2005 Richley
2005/0234555 A1 10/2005 Sutton
2005/0256576 A1 11/2005 Moskowitz et al.
2005/0261683 A1 11/2005 Veldhuizen et al.
2005/0261695 A1 11/2005 Cragg et al.
2005/0277923 A1 12/2005 Sweeney et al.
2005/0278036 A1 12/2005 Leonard
2006/0036322 A1 2/2006 Reiley et al.
2006/0142858 A1 6/2006 Colleran
2006/0149279 A1 7/2006 Mathews
2006/0155297 A1 7/2006 Ainsworth et al.
2006/0167547 A1 7/2006 Suddaby
2006/0217754 A1 * 9/2006 Boehm, Jr. .......... A61B 17/025 606/191
2006/0224241 A1 10/2006 Butler et al.
2006/0287725 A1 12/2006 Miller
2007/0005088 A1 1/2007 Lehuec et al.
2007/0043440 A1 2/2007 William

(56) References Cited

U.S. PATENT DOCUMENTS

| | | | |
|---|---|---|---|
| 2007/0049935 | A1 | 3/2007 | Edidin |
| 2007/0067034 | A1 | 3/2007 | Chiico |
| 2007/0118222 | A1 | 5/2007 | Lang |
| 2007/0167951 | A1 | 7/2007 | Ainsworth et al. |
| 2007/0198089 | A1 | 8/2007 | Moskowitz |
| 2007/0219634 | A1 | 9/2007 | Greenhalgh |
| 2007/0233153 | A1* | 10/2007 | Shipp .................... A61F 2/4611 606/99 |
| 2007/0260315 | A1 | 11/2007 | Foley |
| 2007/0270855 | A1 | 11/2007 | Partin |
| 2007/0276406 | A1 | 11/2007 | Mahoney et al. |
| 2007/0282449 | A1 | 12/2007 | de Villiers |
| 2008/0033440 | A1 | 2/2008 | Moskowitz |
| 2008/0045968 | A1 | 2/2008 | Yu |
| 2008/0082167 | A1 | 4/2008 | Edidin |
| 2008/0108990 | A1 | 5/2008 | Mitchell |
| 2008/0114367 | A1 | 5/2008 | Meyer |
| 2008/0147018 | A1 | 6/2008 | Squilla et al. |
| 2008/0167657 | A1 | 7/2008 | Greenhalgh |
| 2008/0177275 | A1* | 7/2008 | Wing .................... A61F 2/4611 606/99 |
| 2008/0183204 | A1 | 7/2008 | Greenhal et al. |
| 2008/0195153 | A1 | 8/2008 | Altarac |
| 2008/0219604 | A1 | 9/2008 | Chen |
| 2008/0221686 | A1 | 9/2008 | Ferree |
| 2008/0243255 | A1 | 10/2008 | Butler |
| 2008/0249604 | A1 | 10/2008 | Donovan |
| 2008/0281346 | A1 | 11/2008 | Greenhalgh |
| 2008/0287957 | A1* | 11/2008 | Hester .................. A61B 17/025 606/99 |
| 2008/0288072 | A1 | 11/2008 | Kohm |
| 2008/0288078 | A1 | 11/2008 | Kohm |
| 2008/0319549 | A1 | 12/2008 | Greenhalgh |
| 2009/0030423 | A1* | 1/2009 | Puno ..................... A61F 2/4611 606/86 A |
| 2009/0076607 | A1 | 3/2009 | Aalsma |
| 2009/0118771 | A1 | 5/2009 | Gonzalez-Hernandez |
| 2009/0157084 | A1 | 6/2009 | Aalsma |
| 2009/0198338 | A1 | 8/2009 | Phan |
| 2009/0222093 | A1 | 9/2009 | Liu |
| 2009/0222100 | A1 | 9/2009 | Cipoletti |
| 2009/0254129 | A1 | 10/2009 | Tipirneni et al. |
| 2009/0281551 | A1 | 11/2009 | Frey |
| 2009/0281628 | A1 | 11/2009 | Oglaza |
| 2010/0003638 | A1 | 1/2010 | Collins et al. |
| 2010/0016973 | A1 | 1/2010 | De Villiers et al. |
| 2010/0036440 | A1 | 2/2010 | Morris et al. |
| 2010/0049244 | A1 | 2/2010 | Cohen et al. |
| 2010/0069912 | A1* | 3/2010 | McCormack ........ A61B 17/025 606/90 |
| 2010/0082109 | A1 | 4/2010 | Greenhalgh |
| 2010/0160983 | A1* | 6/2010 | Runco ................... A61F 2/4611 606/86 A |
| 2010/0185291 | A1 | 7/2010 | Jimenez |
| 2010/0222784 | A1* | 9/2010 | Schwab ................ A61F 2/4611 606/86 A |
| 2010/0249720 | A1 | 9/2010 | Biyani |
| 2010/0285783 | A1 | 11/2010 | Huguet et al. |
| 2010/0286783 | A1 | 11/2010 | Lechmann |
| 2010/0305705 | A1 | 12/2010 | Butler |
| 2010/0318127 | A1 | 12/2010 | Phan |
| 2010/0331883 | A1 | 12/2010 | Schmitz et al. |
| 2011/0004307 | A1 | 1/2011 | Ahn |
| 2011/0034777 | A1* | 2/2011 | Ames ................. A61B 17/7077 600/206 |
| 2011/0034925 | A1 | 2/2011 | Tipirneni et al. |
| 2011/0035011 | A1 | 2/2011 | Cain et al. |
| 2011/0040329 | A1 | 2/2011 | Ainsworth et al. |
| 2011/0087294 | A1 | 4/2011 | Reiley et al. |
| 2011/0106172 | A1 | 5/2011 | Wallenstein et al. |
| 2011/0125270 | A1 | 5/2011 | Paul |
| 2011/0144703 | A1 | 6/2011 | Krause et al. |
| 2011/0172774 | A1 | 7/2011 | Varela |
| 2011/0184422 | A1 | 7/2011 | Mathews |
| 2011/0224738 | A1 | 9/2011 | Sucec et al. |
| 2011/0270396 | A1 | 11/2011 | Leibowitz |
| 2011/0276141 | A1 | 11/2011 | Caratsch |
| 2011/0282378 | A1 | 11/2011 | Murphy et al. |
| 2011/0282453 | A1 | 11/2011 | Greenhalgh |
| 2011/0301712 | A1 | 12/2011 | Palmatier et al. |
| 2011/0319946 | A1 | 12/2011 | Levy et al. |
| 2011/0319997 | A1 | 12/2011 | Glerum |
| 2012/0004732 | A1 | 1/2012 | Goel |
| 2012/0053642 | A1 | 3/2012 | Lozier |
| 2012/0071977 | A1 | 3/2012 | Oglaza |
| 2012/0083887 | A1 | 4/2012 | Purcell |
| 2012/0083889 | A1 | 4/2012 | Purcell |
| 2012/0101579 | A1* | 4/2012 | de Villiers ............ A61F 2/4611 623/17.16 |
| 2012/0123546 | A1 | 5/2012 | Medina |
| 2012/0130161 | A1* | 5/2012 | Lauryssen ............. A61F 2/4611 600/104 |
| 2012/0136442 | A1 | 5/2012 | Kleiner |
| 2012/0150241 | A1 | 6/2012 | Ragab |
| 2012/0185047 | A1 | 7/2012 | Wooley |
| 2012/0185049 | A1 | 7/2012 | Varela |
| 2012/0209386 | A1 | 8/2012 | Triplett et al. |
| 2012/0215313 | A1 | 8/2012 | Saidha |
| 2012/0215316 | A1 | 8/2012 | Mohr |
| 2012/0226357 | A1 | 9/2012 | Varela |
| 2012/0245689 | A1* | 9/2012 | Gimbel ................. A61F 2/4425 623/17.16 |
| 2012/0245691 | A1 | 9/2012 | Reimels |
| 2012/0271421 | A1* | 10/2012 | Lee ....................... A61F 2/4611 623/17.16 |
| 2013/0006361 | A1 | 1/2013 | Glerum et al. |
| 2013/0053902 | A1 | 2/2013 | Trudeau et al. |
| 2013/0079882 | A1 | 3/2013 | Wolfe |
| 2013/0079883 | A1 | 3/2013 | Butler |
| 2013/0103103 | A1 | 4/2013 | Mire et al. |
| 2013/0103156 | A1 | 4/2013 | Packer et al. |
| 2013/0144391 | A1 | 6/2013 | Siegal |
| 2013/0158669 | A1 | 6/2013 | Sungarian |
| 2013/0190876 | A1 | 7/2013 | Dochner et al. |
| 2013/0190877 | A1 | 7/2013 | Medina |
| 2013/0211526 | A1 | 8/2013 | Alheidt et al. |
| 2013/0231747 | A1 | 9/2013 | Olmos et al. |
| 2013/0310939 | A1 | 11/2013 | Fabian |
| 2013/0325075 | A1 | 12/2013 | Jackson et al. |
| 2013/0325128 | A1 | 12/2013 | Perloff et al. |
| 2014/0012383 | A1 | 1/2014 | Triplett et al. |
| 2014/0031940 | A1 | 1/2014 | Banouskou |
| 2014/0039264 | A1* | 2/2014 | Heiman ............. A61B 17/0218 600/210 |
| 2014/0039622 | A1 | 2/2014 | Glerum |
| 2014/0052253 | A1 | 2/2014 | Perloff et al. |
| 2014/0088714 | A1 | 3/2014 | Miller |
| 2014/0094916 | A1 | 4/2014 | Glerum et al. |
| 2014/0114312 | A1 | 4/2014 | Krause |
| 2014/0121774 | A1 | 5/2014 | Glerum et al. |
| 2014/0128977 | A1 | 5/2014 | Glerum |
| 2014/0142639 | A1 | 5/2014 | Vennard et al. |
| 2014/0163683 | A1 | 6/2014 | Seifert et al. |
| 2014/0172027 | A1 | 6/2014 | Biedermann et al. |
| 2014/0172106 | A1 | 6/2014 | To et al. |
| 2014/0188180 | A1 | 7/2014 | Biedermann et al. |
| 2014/0188224 | A1 | 7/2014 | Dmuschewsky |
| 2014/0194991 | A1 | 7/2014 | Jimenez |
| 2014/0194992 | A1 | 7/2014 | Medina |
| 2014/0249631 | A1 | 9/2014 | Weiman |
| 2014/0257484 | A1 | 9/2014 | Flower |
| 2014/0277139 | A1 | 9/2014 | Vrionis et al. |
| 2014/0277460 | A1* | 9/2014 | Schifano ............ A61B 17/8605 606/86 R |
| 2014/0277486 | A1* | 9/2014 | Abdou .................. A61F 2/4465 623/17.16 |
| 2014/0277490 | A1 | 9/2014 | Perloff |
| 2014/0277497 | A1 | 9/2014 | Bennett et al. |
| 2014/0303730 | A1 | 10/2014 | Mcguire et al. |
| 2014/0324044 | A1 | 10/2014 | Haufe et al. |
| 2014/0343559 | A1* | 11/2014 | Flickinger .............. A61B 17/88 606/90 |

(56) References Cited

U.S. PATENT DOCUMENTS

| | | | | |
|---|---|---|---|---|
| 2014/0379086 | A1 | 12/2014 | Elahinia | |
| 2015/0012048 | A1 | 1/2015 | Huebner et al. | |
| 2015/0012098 | A1 | 1/2015 | Eastlack | |
| 2015/0018951 | A1 | 1/2015 | Loebl | |
| 2015/0066039 | A1* | 3/2015 | Siegal | A61B 17/0218 606/90 |
| 2015/0066145 | A1 | 3/2015 | Rogers et al. | |
| 2015/0073552 | A1 | 3/2015 | To | |
| 2015/0080973 | A1* | 3/2015 | Eastlack | A61B 17/025 606/86 A |
| 2015/0257746 | A1* | 9/2015 | Seifert | A61B 17/3462 600/206 |
| 2015/0265320 | A1 | 9/2015 | Hynes et al. | |
| 2015/0342586 | A1 | 12/2015 | Lim et al. | |
| 2016/0030029 | A1 | 2/2016 | Mahoney et al. | |
| 2016/0051373 | A1 | 2/2016 | Faulhaber | |
| 2016/0120532 | A1* | 5/2016 | Donald | A61B 17/0293 600/210 |
| 2016/0128846 | A1 | 5/2016 | Voellmicke | |
| 2016/0199194 | A1 | 7/2016 | Slater et al. | |
| 2016/0270772 | A1 | 9/2016 | Beale et al. | |
| 2016/0278791 | A1 | 9/2016 | Pellegrino et al. | |
| 2016/0287322 | A1* | 10/2016 | Solsberg | A61B 17/3421 |
| 2016/0310190 | A1 | 10/2016 | Gonzalez et al. | |
| 2016/0310291 | A1 | 10/2016 | Greenhalgh | |
| 2016/0338846 | A1 | 11/2016 | Walker | |
| 2017/0042695 | A1 | 2/2017 | Foley et al. | |
| 2017/0056200 | A1 | 3/2017 | Koch et al. | |
| 2017/0065269 | A1 | 3/2017 | Thommen et al. | |
| 2017/0105845 | A1 | 4/2017 | Glerum et al. | |
| 2017/0112631 | A1 | 4/2017 | Kuyler | |
| 2017/0202684 | A1* | 7/2017 | Padovani | A61F 2/4611 |
| 2017/0238788 | A1 | 8/2017 | Jackson | |
| 2017/0258605 | A1 | 9/2017 | Blain et al. | |
| 2017/0281365 | A1* | 10/2017 | Robinson | A61B 17/0206 |
| 2018/0014866 | A1 | 1/2018 | Vrionis et al. | |
| 2018/0071000 | A1 | 3/2018 | Pham et al. | |
| 2018/0078384 | A1 | 3/2018 | Suddaby | |
| 2018/0092677 | A1 | 4/2018 | Peterson et al. | |
| 2018/0092751 | A1 | 4/2018 | Vrionis et al. | |
| 2018/0160923 | A1 | 6/2018 | Spangler et al. | |
| 2018/0193164 | A1 | 7/2018 | Shoshtaev | |
| 2018/0206897 | A1 | 7/2018 | Palmer | |
| 2018/0250051 | A1 | 9/2018 | Vrionis et al. | |
| 2018/0310975 | A1 | 11/2018 | Haufe et al. | |
| 2019/0038435 | A1 | 2/2019 | Daffinson et al. | |
| 2019/0046328 | A1 | 2/2019 | Rosenwasser et al. | |
| 2019/0142407 | A1 | 5/2019 | Jung et al. | |
| 2019/0142408 | A1 | 5/2019 | Jung et al. | |
| 2019/0209154 | A1 | 7/2019 | Richter et al. | |
| 2019/0328543 | A1 | 10/2019 | Lin et al. | |
| 2020/0015925 | A1 | 1/2020 | Scheib | |
| 2020/0069435 | A1 | 3/2020 | Eastlack et al. | |
| 2020/0085586 | A1 | 3/2020 | Ludwig et al. | |
| 2020/0107824 | A1 | 4/2020 | Fleischer | |
| 2020/0179632 | A1 | 6/2020 | Worley | |
| 2020/0246162 | A1* | 8/2020 | Schultz | A61F 2/4455 |
| 2020/0360150 | A1* | 11/2020 | Patel | A61B 17/7064 |
| 2020/0383675 | A1 | 12/2020 | Jung | |
| 2021/0068863 | A1 | 3/2021 | Choi et al. | |
| 2021/0077275 | A1* | 3/2021 | Milella, Jr. | A61F 2/4465 |
| 2021/0259855 | A1* | 8/2021 | Kang | A61F 2/4611 |
| 2021/0315710 | A1 | 10/2021 | Koch et al. | |
| 2021/0330472 | A1 | 10/2021 | Shoshtaev | |
| 2022/0039969 | A1* | 2/2022 | Milella, Jr. | A61B 17/8805 |
| 2022/0175418 | A1 | 6/2022 | Ebersole et al. | |
| 2024/0009003 | A1* | 1/2024 | Barba | A61B 17/3423 |
| 2025/0195113 | A1* | 6/2025 | Heo | A61B 17/7061 |
| 2025/0248715 | A1* | 8/2025 | Sand | A61B 17/1617 |

FOREIGN PATENT DOCUMENTS

| | | | |
|---|---|---|---|
| CA | 2567274 | 11/2014 | |
| CN | 105636555 | 6/2016 | |
| CN | 108024860 | 5/2018 | |
| EP | 0260044 | 3/1988 | |
| EP | 1006956 | 6/2000 | |
| EP | 2693989 | 2/2014 | |
| EP | 2729092 | 5/2014 | |
| EP | 2793760 | 10/2014 | |
| EP | 3016617 | 5/2016 | |
| EP | 3038565 | 7/2016 | |
| EP | 3038566 | 7/2016 | |
| JP | 2004536657 | 12/2004 | |
| JP | 2007521886 | 8/2007 | |
| JP | 2011519673 | 7/2011 | |
| JP | 6096282 | 2/2017 | |
| JP | 2018525131 | 9/2018 | |
| KR | 101852973 | 5/2018 | |
| WO | 1998034568 | 8/1998 | |
| WO | 2000025706 | 5/2000 | |
| WO | 2002076335 | 10/2002 | |
| WO | 2003032812 | 4/2003 | |
| WO | 2005112834 | 12/2005 | |
| WO | 2008070863 | 6/2008 | |
| WO | 2009037509 | 3/2009 | |
| WO | 2009092102 | 7/2009 | |
| WO | 2010078468 | 7/2010 | |
| WO | 2010105181 | 9/2010 | |
| WO | 2012047712 | 4/2012 | |
| WO | 2012112596 | 8/2012 | |
| WO | 2012141715 | 10/2012 | |
| WO | 2013052807 | 4/2013 | |
| WO | 2013109346 | 7/2013 | |
| WO | 2013173767 | 11/2013 | |
| WO | 2014144696 | 9/2014 | |
| WO | 2014151162 | 9/2014 | |
| WO | 2014164625 | 10/2014 | |
| WO | 2015009998 | 1/2015 | |
| WO | 2015031291 | 3/2015 | |
| WO | 2015063719 | 5/2015 | |
| WO | 2017015165 | 1/2017 | |
| WO | 2017027277 | 2/2017 | |
| WO | 2017035155 | 3/2017 | |
| WO | 2017051416 | 3/2017 | |
| WO | 2021050577 | 3/2021 | |
| WO | 2021241890 | 12/2021 | |
| WO | WO-2023141617 A1 * | 7/2023 | A61B 17/1775 |

OTHER PUBLICATIONS

U.S. Appl. No. 18/464,949, filed Sep. 11, 2023, Drive Instruments With Retention Mechanisms, Medical Implants, and Related Technologies.

U.S. Appl. No. 18/596,610, filed Mar. 5, 2024, Expandable Interbody Devices and Instruments.

U.S. Appl. No. 18/393,600, filed Dec. 21, 2023, Bone Fusion System.

U.S. Appl. No. 18/931,395, filed Oct. 30, 2024, Expandable Intervertebral Cage.

Choi, Chang Myong et al. "How I do it? Biportal endoscopic spinal surgery (BESS) for treatment of lumbar spinal stenosis." Acta Neurochir (2016) 158:459-463; published Jan. 18, 2016.

Eum, Jin Hwa et al. "Percutaneous biportal endoscopic decompression for lumbar spinal stenosis: a technical note and preliminary clinical results." J Neurosurg Spine 24:602-607, Apr. 2016; published online Jan. 1, 2016.

Innovasive Inc. "Innovasive DualX LLIP expanding IBFD Product Information and Instructions for Use." May 2018, 2 pages.

International Bureau, Written Opinion, PCT Patent Application PCT/US2016/048222 filed Aug. 23, 2016; mailed Mar. 2, 2017, 4 pages.

ISA, International Search Report and Written Opinion, PCT Patent Application PCT/US2020/049982, mailed Jan. 26, 2021, 21 pages.

Kim, Jin-Sung et al., "Endoscope-assisted oblique lumbar interbody fusion for the treatment of cauda equina syndrome: a technical note." Eur Spine J (2017) 26:397-403.

International search Report and Written Opinion for PCT/US2021/063881 mailed May 4, 2022, 32 pages.

(56) References Cited

OTHER PUBLICATIONS

European Search Report for Application No. Patent No. 21907844.1-1122 / 4262636 PCT/US2021063881 mailed Oct. 14, 2024, 9 pages.
International Preliminary Report on Patentability and International Search Report and Written Opinion for Application No. PCT/US2022/019706 mailed Sep. 21, 2023, 8 pages.
European Search Report for Application No. 20863847.8, 7 pages.
Japanese Office Action for Application No. 2022-541192 mailed Mar. 11, 2024, 10 pages with English translation.
International Search Report and Written Opinion for PCT/US2023/081937 mailed May 8, 2024, 16 pages.
First Examination Report for Application No. 20863847.8 mailed Sep. 12, 2024, 4 pages.
First Office Action for Chinese Application No. 202080078070.2 mailed Sep. 20, 2024, 40 pages with English translation.
International Preliminary Report on Patentability, PCT Patent Application No. PCT/US2020/049982 mailed Mar. 17, 2022, 17 pages.
Final Office Action mailed Jul. 20, 2020 in U.S. Appl. No. 16/043,116, 7 pages.
Non-Final Office Action mailed Dec. 19, 2019 in U.S. Appl. No. 16/043,116, 8 pages.
Non-Final Office Action mailed Jun. 12, 2018 in U.S. Appl. No. 15/244,446, 9 pages.
Notice of Allowance mailed Jul. 13, 2018 in U.S. Appl. No. 15/244,446, 5 pages.
Notice of Allowance mailed Sep. 22, 2020 in U.S. Appl. No. 16/043,116, 5 pages.
International Search Report and Written Opinion, PCT Patent Application PCT/US2024/018567, mailed Aug. 8, 2024, 26 pages.
Office Action of U.S. Appl. No. 16/443,302, mailed Feb. 3, 2021, 34 pages.
Office Action issued for U.S. Appl. No. 15/970,212, dated Sep. 24, 2020, 16 pages.
Final Office Action issued in U.S. Appl. No. 15/718,786, mailed Mar. 19, 2020.
Notice of Allowance issued for U.S. Appl. No. 15/970,212, dated Jun. 3, 2021, 6 pages.
International Preliminary Report on Patentability and Written Opinion, dated Jun. 21, 2016, received in connection with International Patent Application No. PCT/US2014/070899, 1 page.
International Search Report and Written Opinion, dated May 14, 2015, received in connection with International Patent Application No. PCT/US2014/070899, 15 pages.
International Preliminary Report on Patentability and Written Opinion, dated Apr. 8, 2014, received in connection with International Patent Application No. PCT/US2012/0589681, 1 page.
International Search Report and Written Opinion for PCT/US2012/058968 mailed Mar. 28, 2013, 17 pages.
International Preliminary Report on Patentability issued in PCT/US2015/043109, mailed Feb. 16, 2017, 2 pages.
International Search Report and Written Opinion for issued in PCT/US2015/043109, mailed Nov. 2, 2015, 8 pages.
International Search Report and Written Opinion for Application No. PCT/US2022/019706 mailed Jun. 20, 2022, 13 pages.
International Search Report and Written Opinion for Application No. PCT/US2020/049982 mailed Jan. 26, 2021, 21 pages.
Zimmer® Herbert™ Cannulated Bone Screw, Webpage, http://www.zimmerbiomet.com/content/dam/zimmer-biomet/medicalprofessionals/000-surgical-techniques/trauma/zimmer-herbert-cannulated-bone-screw.pdf, dated Jul. 27, 2015, accessed Jan. 2, 2018.

* cited by examiner

SPINAL IMPLANT DELIVERY DEVICE FOR PROTECTING TISSUE

CROSS-REFERENCE TO RELATED APPLICATION

The present application claims the benefit of U.S. Provisional Patent Application No. 63/611,913, filed Dec. 19, 2023, the disclosure of which is incorporated herein by reference in its entirety.

TECHNICAL FIELD

The present disclosure relates generally to medical systems and, more particularly, to systems, devices, and methods for delivering implants while protecting tissue, such as nerve tissue.

BACKGROUND

Individuals often suffer from damaged or displaced spinal discs and/or vertebral bodies due to trauma, disease, degenerative defects, or wear over an extended period of time. One result of this displacement or damage to a spinal disc or vertebral body may be chronic back pain. A common procedure for treating damage or disease of the spinal disc or vertebral body may involve partial or complete removal of an intervertebral disc. An intervertebral implant (commonly referred to as an interbody spacer or cage) can be inserted into the cavity created where the intervertebral disc was removed to help maintain height of the spine and/or restore stability to the spine. An interbody spacer may also provide a lordotic correction to the curvature of the spine. An example of an interbody spacer that has been commonly used is a fixed dimension cage, which typically is filled with bone and/or bone growth-inducing materials. Unfortunately, it may be difficult to implant the interbody spacer at the intended implantation site between vertebral bodies. Additionally, conventional surgical techniques can cause a significant amount of trauma at or near the implantation site (e.g., injury to nerve tissue), which can significantly increase recovery time and/or lead to patient discomfort. Accordingly, there is a need for improved surgical systems, visualization techniques, and/or related technologies for delivering a spinal implant.

DETAILED DESCRIPTION

Figure 1A:
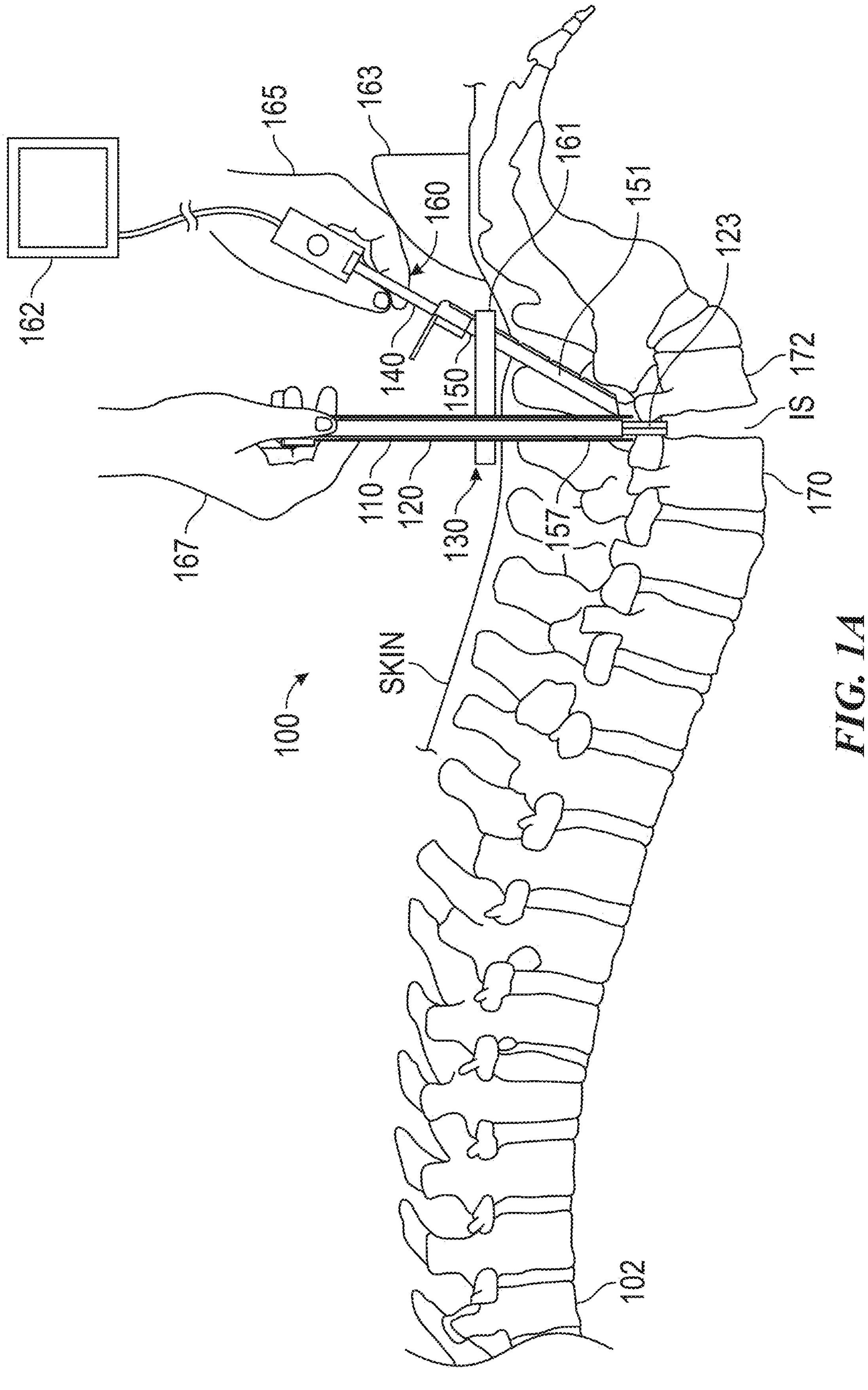
FIG. 1A is a side view of a spinal surgical system in accordance with an embodiment of the disclosure.

The following disclosure describes various embodiments of delivery devices and associated systems and methods of use. The delivery device can include slotted or elongated split delivery guide that can be inserted into a subject towards, for example, an intervertebral space or other target site for delivering one or more spinal implants. The split elongated delivery guide can include spaced apart insertion members defining a channel along which implants can be passed. The insertion members can be compressed (e.g., pushed towards each other) for insertion into the patient. When uncompressed, sidewalls of the insertion members can extend in parallel directions and define a generally U-shaped delivery channel through which a spinal implant can be delivered. The insertion members can each have a geometry (e.g., an L-shaped cross-section) that defines a channel sidewall and channel bottom. The channel sidewalls can define an upper opening of the channel. The insertion members thereby protect adjacent tissue and nerves from potential damage while the implant is delivered along the channel. For example, the delivery device can be oriented such that the protected side or face of the delivery devices faces a particular area of the subject's tissue (e.g., nerve tissue), organs, vascular features, or the like. In another example, the device can be inserted into the subject with the protected side facing the spinal cord to deliver an intervertebral cage distally past the spinal cord and into the disc space. The split elongated delivery guide can prevent physical contact between the cage and the spinal cord.

In some embodiments, the insertion members include distance indicators and/or a plurality of apertures. The distance indicators can be used to visually determine how deep the insertion members are inserted into a subject at any given time. The apertures can provide a direct view into the channel of the spinal implant delivery device, allowing a surgeon or other user to visually determine the position of an instrument or implant disposed in the channel. In some embodiments, the apertures are aligned with the distance indicators such that the surgeon or other user can more accurately determine the position of the instrument or implant.

The spinal implant delivery device can be included in a spinal surgical system that also includes a visualization instrument, which can help a user identify tissue and operate the spinal implant delivery device while preventing or limiting injury or damage to non-targeted organs and tissues. In endoscopic-assisted surgeries, instruments and implantable devices can be precisely positioned using minimally invasive techniques to improve outcomes and reduce recovery times. Certain details are set forth in the following description and in the figures to provide a thorough understanding of such embodiments of the disclosure. Other details describing well-known structures and systems often associated with, for example, surgical procedures are not set forth in the following description to avoid unnecessarily obscuring the description of various embodiments of the disclosure.

A. OVERVIEW

At least some embodiments are directed to spinal implant delivery devices and associated spinal surgery systems. The systems, devices, and methods disclosed herein can be used to implant a fixed or expandable interbody device (e.g., devices to space apart vertebral bodies, restore stability of the spine, provide lordotic correction, etc.), or perform other surgical procedures while protecting surrounding tissue and nerves.

In some embodiments, a spinal implant delivery device includes a handle assembly and an elongated split delivery guide coupled to the handle assembly. The elongated split delivery guide can include a first insertion member and a second insertion member extending in the same direction (i.e., parallel to the first insertion member). The first and second insertion members can be spaced apart to define a delivery channel. The first and second insertion members can include L-shaped cross-sections facing each other such that the channel has an opening at the top and a longitudinally-extending slot at the bottom. An instrument or implant disposed in the channel can exit the channel through the opening. The slot can have a sufficiently narrow gap so that an instrument or implant disposed in the channel cannot exit the channel through the bottom. The bottom can thereby prevent the instrument or implant from pressing against tissue or nerves on the other side of the slot, thereby protecting the tissue and nerves. The orientation of the device can be selected so that the slot faces tissue and nerves deemed to be particularly susceptible to damage depending on the type of surgical procedure, the location of the target site, the type of implant to be delivered, the angle at which the device is inserted into the subject, etc. In some embodiments, the handle assembly can assist in manual handling of the device and visually indicate the orientation of the device.

In some embodiments, the device includes distance indicators that can help a surgeon or other user visually determine how deep the device has been inserted into the subject. In some embodiments, the device includes apertures that allow the surgeon or other user to see through and visually determine the position of the implant or instrument disposed in the channel of the device. The apertures can be aligned with the distance indicators so that the position of the implant or instrument can be more accurately determined.

In some embodiments, a method for delivering a spinal implant to a subject's spine includes inserting a spinal implant delivery device in a subject, and delivering a spinal implant to the subject's spine through a chamber defined by the spinal implant delivery device. In some embodiments, the device can include an elongated split delivery device with a pair of insertion members extending longitudinally. The elongated split delivery device can be configured to bias the insertion members to be spaced apart by a particular distance. In some procedures, the elongated split delivery device can be manually squeezed to bring the two insertion members closer to one another prior to insertion of the device into the subject, then released when the device is properly inserted to create an enlarged space for implant delivery.

In some embodiments, the spinal implant delivery device is used in a spinal surgical system that also include a visualization instrument and/or other devices to assist the surgical procedure, including instrument holders, pillows, etc. Surgical techniques described herein can include a spinal implant delivery procedure, a decompression procedure, an oblique lumbar interbody fusion (OLIF) procedure, a lateral lumbar interbody fusion (LLIF) procedure, a posterior lumbar interbody fusion (PLIF) procedure, a transforaminal lumbar interbody fusion (TLIF) procedure, an anterior lumbar interbody fusion (ALIF) procedure, or combinations thereof.

Embodiments of the present disclosure will be described more fully hereinafter with reference to the accompanying drawings in which like numerals represent like elements throughout the several figures, and in which example embodiments are shown. Embodiments of the claims may, however, be embodied in many different forms and should not be construed as limited to the embodiments set forth herein. The examples set forth herein are non-limiting examples and are merely examples among other possible examples.

B. SPINAL SURGICAL SYSTEMS

FIG. 1A a side view of a spinal surgical system 100 ("system 100") positioned along a human subject's spine 102 in accordance with an embodiment of the disclosure. The system 100 can include an instrument assembly 130, a visualization assembly 160, and a multi-portal instrument holder 161 ("instrument holder 161"). The instrument holder 161 can hold the instrument assembly 130 and visualization assembly 160. The instrument holder 161 can be configured to hold components (e.g., cannulas, surgical instruments, combinations thereof, etc.) of the instrument assembly 130, visualization assembly 160, and/or other equipment, such as surgical beds.

The instrument assembly 130 can an implant delivery device 120 ("the device 120") defining a delivery path 121 along which an implant 123 carried by an instrument 110 can be delivered toward the implantation site IS. The device 120 can be slotted or be a split elongated delivery guide that can be inserted into a subject towards, for example, an intervertebral space or other target site for delivering the implant 123. The visualization assembly 160 can include a visualization instrument 140 and a cannula or device 150. In some embodiments, instruments 110, 140 include instruments disclosed in U.S. application Ser. No. 17/902,685 and U.S. Pat. No. 11,678,906. The instruments 110 and 140 can be moved distally and/or laterally out of the devices 120 and 150, respectively, which can be positioned in incisions or endoscopic ports, to access a relatively large working space along the patient's spine 102. In some embodiments, the devices 120 and 150 are identical or generally similar. In other embodiments, the devices 120 and 150 are different. The devices 120, 150 can have longitudinally extending openings along their entire lengths or portion thereof (not fully visible in FIG. 1A) to allow distal portions of the respective instruments 110, 140 to be moved laterally into and out of sides of the devices 120, 150. Positioning of instruments is discussed in connection with FIGS. 6A-8B.

The illustrated device 120 has an open top facing away from the subject's spine (the open side is partially visible and partially obscured by the instrument 110 in FIG. 1A) and a protected side or face opposite the open side and facing the subject's spine (the protected side is not visible in FIG. 1A). The protected side can include a backside atraumatic surface 157 such that contact with the device 120 and/or the instrument 110 limits, reduces, or substantially eliminates trauma to tissue, nerves, and/or other components around the spine 102. A series of instruments can be delivered through the device 120. In some procedures, the instrument 110 can be used to remove tissue (e.g., intervertebral disc, tissue contributing to stenosis, etc.), form access paths to implantation sites, prepare an implantation site by, for example, moving organs or tissue (e.g., moving nerve tissue), prepare vertebral bodies (e.g., roughening or shaping vertebral endplates), or the like. In some embodiments, the device 120 can create an enlarged intervertebral space at the target site, as will be described in further detail herein. An interbody implant can be delivered through the device 120 (e.g., via the instrument 110) to the intervertebral space IS. In some embodiments, a different cannula or device can be used for guiding the instrument 110 while the device 120 is used to deliver the implant 123. In expandable implant embodiments, an expandable interbody fusion implant 123 can be expanded to push apart vertebral endplates.

With continued reference to FIG. 1A, a customizable ergonomic pillow 163 can be used to position a user's body during the surgical procedure. The illustrated pillow 163 is configured to support the user's hand 165 holding the visualization assembly 160. Any number of pillows can be used during the surgical procedure to support the user's other hand 167 or other body parts. Additionally, sets of pillows can be used for corresponding sets for surgical actions. For example, a first set of pillows can be used to perform a first decompression procedure at a first level of the patient's spine, a second set of pillows can be used to perform a second decompression procedure at a second level of the patient's spine, and a third set of pillows can be used to perform one or more implantation procedures at the first and/or second level or other levels. The pillows can be coupled to the patient's body, operating table, and/or other attachment features.

The visualization assembly 160 can provide intraoperative endoscopic viewing of workspaces, delivery paths, organs, tissue (e.g., nerve tissue) implantation sites, implants, interbody fusion devices (e.g., before, during, and/or after delivery), instrument(s) (including dispensers, dilators, decompression instruments, etc.), and other areas or features of interest. The position of the devices 120, 150 can be selected based on the procedure and optical characteristics (e.g., field of view, zoom capability, etc.) of the visualization assembly 160. The visualization assembly 160 can be moved throughout the procedure to provide intraoperative endoscopic viewing of one, multiple, or all of the surgical steps. For example, the visualization assembly 160 can be used to view delivery of the spinal implant along the device 120, tissue contributing to nerve compression caused by narrowing of the spinal canal associated with arthritis of the spine, degeneration of spinal discs, and thickening of ligaments. Arthritis of the spine often leads to the formation of bone spurs, which can narrow the spinal canal and press on the spinal cord. This tissue can be viewed using the visualization assembly 160. In spinal disc degeneration, the visualization assembly 160 can view the inner tissue of the disc protruding through a weakened fibrous outer covering of the disc and pressing on the spinal cord and/or spinal nerve roots. The protruding tissue can be viewed before and/or during removal. The visualization assembly 160 can be used to also view ligaments pressing on the spinal cord and/or nerve roots to assist in treatment.

The visualization instrument 140 can be a low-profile fiber-optic endoscope positioned directly through an incision, an endoscopic port, or the like. The visualization instrument 140 can include one or more endoscopes having, without limitation, fiber optics (e.g., optical fibers), lenses, imaging devices, working lumens, light source controls, or the like for direct viewing or viewing via a display 162 (e.g., an electronic screen, a monitor, etc.). In some embodiments, the visualization instrument 140 can include a lumen through which fluid flows to irrigate the surgical site. For example, saline, or another suitable liquid, can be pumped through the visualization instrument 140 to remove tissue (e.g., loose tissue, bone dust, etc.) or other material impairing visualization. The visualization instrument 140 can also include one or more lumens (e.g., irrigation return lumens, vacuum lumens, etc.) through which the irrigation liquid can be withdrawn.

The visualization instrument 140 can illuminate the body cavity and enable high-resolution video visualization. A light source (e.g., a laser, light-emitting diode, etc.) located near or at the proximal end of the fiber optics can be used to transmit light to the distal end and provide illuminating light. This enables a surgeon to safely navigate into the subject's body and to illuminate specific body anatomy to view vertebral spacing, vertebral structures, nerves, bony buildup (e.g., buildup that could be irritating and pressing against nerves contributing to nerve compression), etc. This also allows a surgeon to illuminate portions of the device 120 and view a position of an implant along the length of the device 120. In some embodiments, visualization optics for vision and illumination are included within the distal tip of the visualization instrument 140. The configuration and functionality of the visualization instrument 140 can be selected based on the desired field of view, viewing resolution, pan/zoom functionality, or the like. Irrigation techniques, visualization devices, instruments, cannulas, and visualization and surgical techniques are discussed in U.S. application Ser. No. 17/902,685 and U.S. application Ser. No. 16/687,520, which are incorporated by reference in their entireties.

To position the devices 120, 150, the devices 120, 150 can be inserted into entrances formed in the subject's skin. The multi-portal instrument holder 161 can be adjusted to hold the devices 120, 150 at the fixed or altered positions while instruments (e.g., instruments 110, 140) are delivered through the devices 120, 150. The instrument holder 161 can be used to set the distance between the devices 120, 150 and can be locked to hold the devices at, for example, a set distance and/or angular orientation. For example, the instrument holder 161 can have locking mechanisms that are locked by the user to hold the devices 120, 150 stationary relative to one another. The instrument holder 161 can be unlocked to reposition the devices. This process can be performed any number of times to reposition the devices 120, 150.

The instrument holder 161 can also be used to hold the instruments 110, 140 in a similar manner. In some embodiments, an instrument holder or devices 120, 150 and another multi-portal instrument holder holds the instruments 110, 140. This allows for flexibility during the surgical procedure to hold various components stationary relative to one another when desired. For example, a multi-portal instrument holder in the form of a triangulation guide can be used with the instruments 110, 140. A multi-portal instrument holder can hold the devices 120, 150 stationary relative to one another. This allows for some instruments to be moved relative to one another while other instruments are held relatively stationary.

Figure 1B:
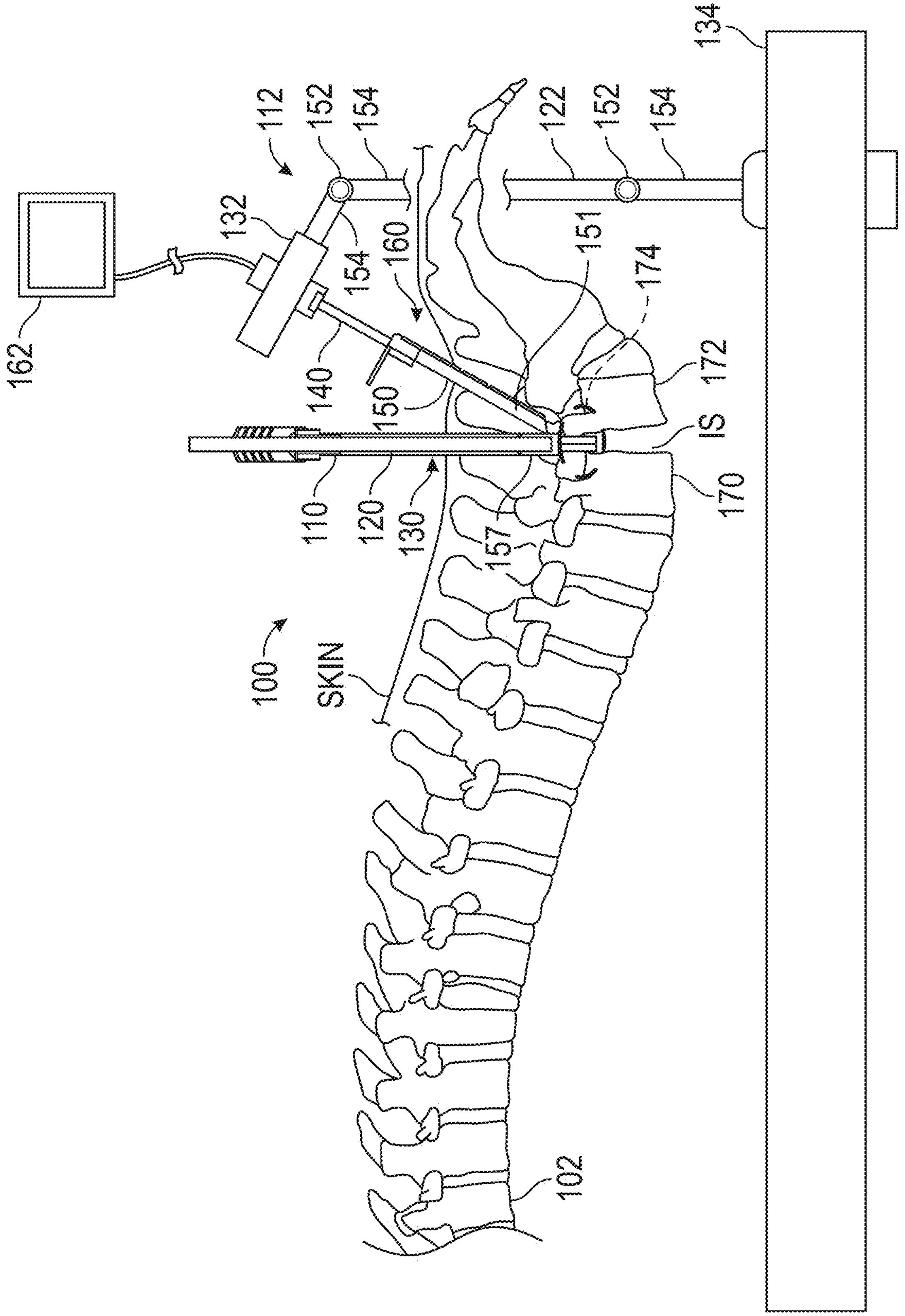
FIG. 1B is a side view of a spinal surgical system in accordance with another embodiment of the disclosure.

FIG. 1B is a side view of the spinal surgical system 100 in accordance with another embodiment of the disclosure. The system 100 of FIG. 1B is generally similar to the system

100 of FIG. 1A except as detailed below. The system 100 can include an instrument holder 112 having an arm 122 configured to be coupled to a structure 134 (e.g., surgical bed, a mounting bar, etc.) via, for example, one or more clamps, and a clamp or jaw 132 ("jaw 132") coupled to the arm 122. The jaw 132 is configured to grip the visualization instrument 140 when the arm 122 is at a fixed configuration, thereby holding the visualization instrument 140 stationary relative to a patient. The arm 122 can include one or more joints (e.g., manual joints, motorized joints, etc.), linkages, motors, controllers, sensors, or the like. The configuration of the arm 122 can be selected based on the desired range of motion, degrees of freedom, or the like. In some embodiments, the arm 122 includes multiple joints 152 and linkages 154. The number of linkages, joints, and other components of the arm 122 can be selected based on the desired positioning of the instrument and range of motion.

Figure 2B:
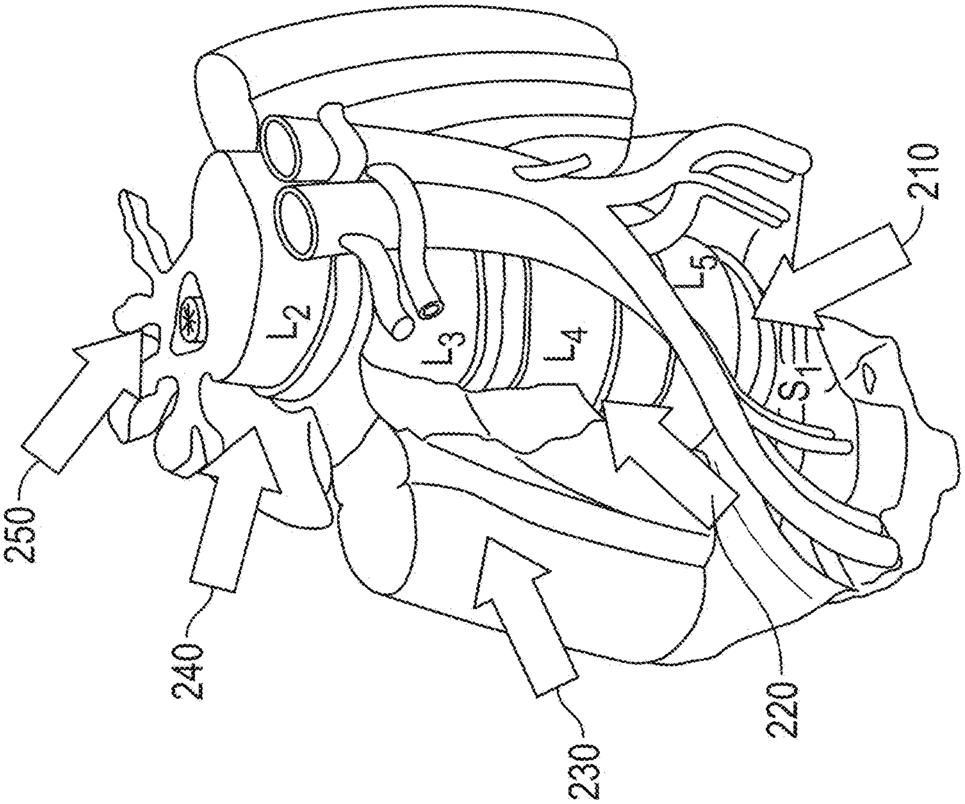
FIG. 2B is an isometric view of the lumbar spine of FIG. 2A.
Figure 2A:
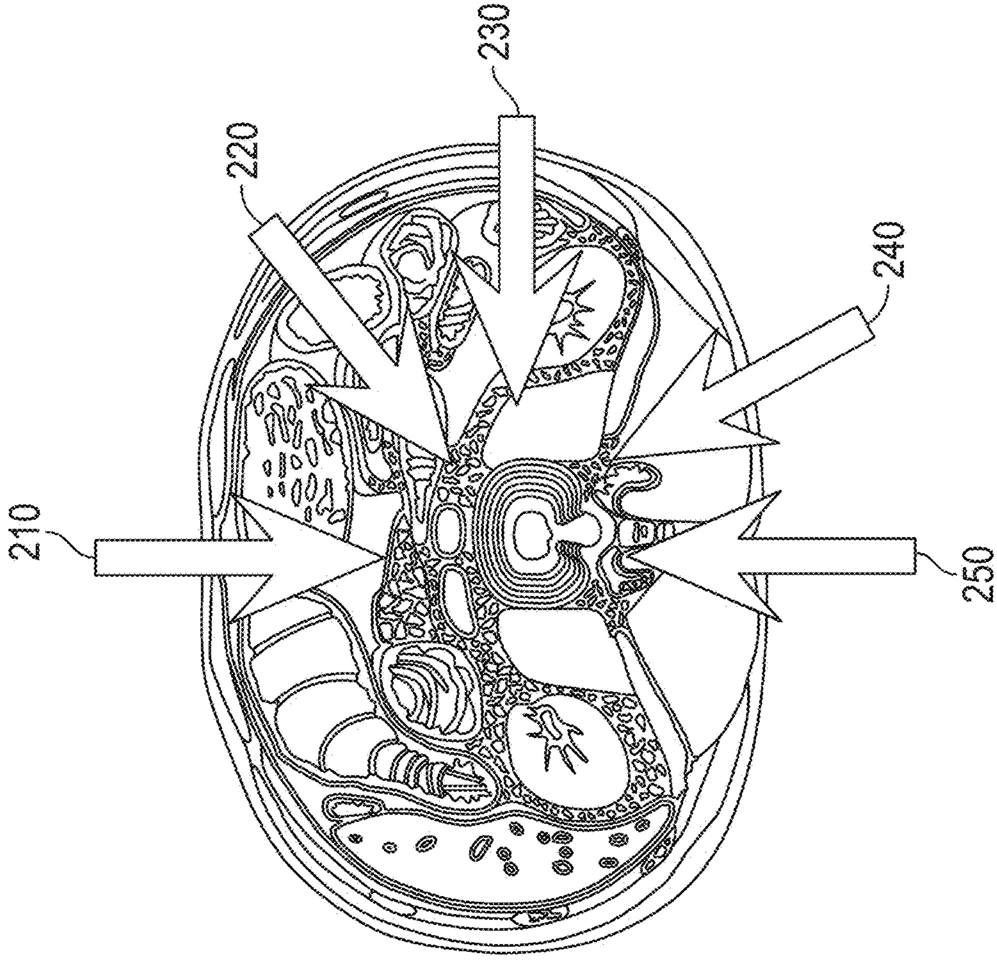
FIG. 2A is a schematic top plan view showing surgical approaches to a lumbar spine for performing procedures.

FIG. 2A is a schematic top plan view showing surgical approaches to a lumbar spine for performing procedures. FIG. 2B is an isometric view of the lumbar spine of FIG. 2A. The surgical approaches illustrated can be for performing procedures suitable for the system 100 of FIGS. 1A and 1B, and other systems disclosed herein. The number and configuration of physician-support pillows can be selected based on the spinal approach.

Referring to FIGS. 2A and 2B together, surgical equipment (e.g., the device 120) can be delivered via different paths, including an ALIF path 210, an OLIF path 220, an LLIF or extreme lateral lumbar interbody fusion (XLIF) path 230, a TLIF path 240, and a PLIF path 250. These paths can be used to deliver spinal implants to a target site on a subject's spine. These paths can also be used to perform other procedures disclosed herein. For example, one or more of the paths 210, 220, 230 240, 250 can be selected for multi-portal endoscopic approaches to perform a wider array of lumbar spine procedures than conventional one-portal techniques. Devices can be positioned along the same path or different paths to allow for independent positioning and manipulation of the endoscopic camera of the surgical instruments, thereby providing greater flexibility and enhanced visualization of spinal anatomy.

Surgical instruments can remove tissue to define working space(s) inside the patient. In one example TLIF procedure, the transforaminal path 240 may be employed to implant a single small expandable or non-expandable interbody spacer at the intervertebral space. In one example PLIF procedure, two interbody spacers can be delivered along the posterior path 250 and implanted at the intervertebral space. The two interbody spacers can cooperate to keep the vertebral bodies at the desired spacing and may be larger than the TLIF spacer. Additionally, multiple interbody spacers can provide lordotic correction by providing support at different heights. In one example LLIF procedure, a single, relatively large interbody spacer can be delivered along the lateral path 230 and implanted to provide asymmetrical support. In one example ALIF procedure, an asymmetric interbody spacer can be delivered along the anterior path 210 to provide support consistent with lordosis at that portion of the spine. Lateral approaches, transforaminal approaches, and anterior approaches can be used to access the cervical spine, thoracic spine, etc. The number of instruments, configurations of instruments, implants, and surgical techniques can be selected based on the condition to be treated.

FIGS. 3A, 3B, 3C, and 3D are front isometric, rear isometric, top, and bottom views, respectively, of the implant delivery device 120 in accordance with an embodiment of the disclosure. Referring first to FIGS. 3A-3D together, the device 120 includes a handle assembly 340 and an elongated split delivery guide 310 (e.g., having a slotted channel member) coupled to the handle assembly 340 and defining a delivery channel 350 (e.g., an implant delivery channel). The elongated split delivery guide 310 can include a pair of cantilevered fingers, including a first insertion member 320 and a second insertion member 330 extending in a direction along a longitudinal axis L-L. The elongated split delivery guide 310 (including the first and second insertion members 320, 330) can be made from surgical- and/or medical-grade materials including metal (e.g., stainless steel, titanium), plastics, silicone, and/or other suitable materials. The handle assembly 340 can be made from metal, plastics, silicone, and/or other suitable materials.

Figure 3A:
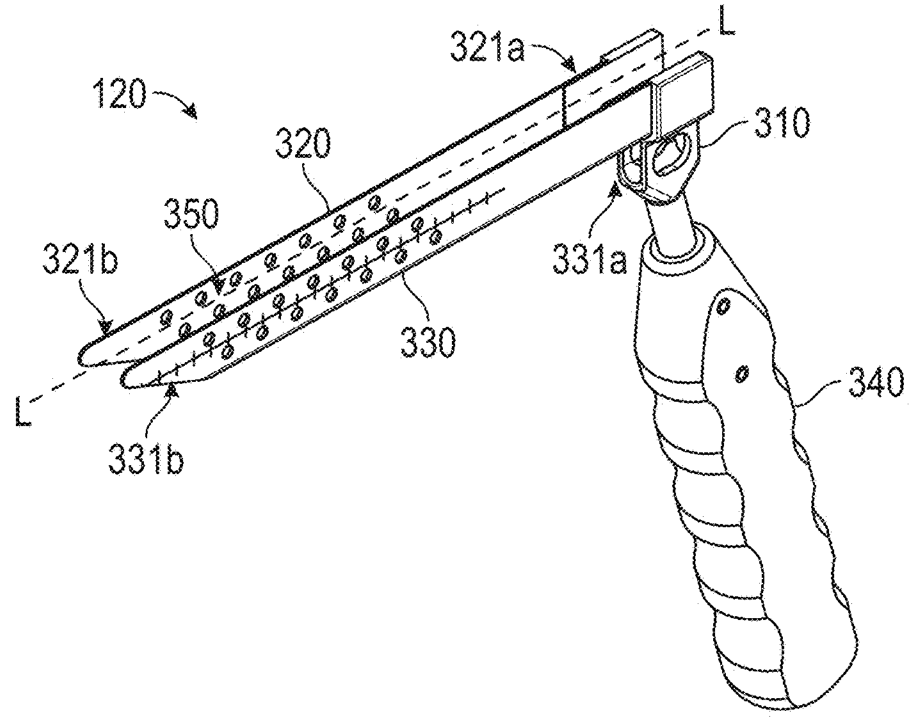
FIGS. 3A, 3B, 3C, and 3D are front isometric, rear isometric, top, and bottom views, respectively, of a spinal implant delivery device in accordance with an embodiment of the disclosure.
Figure 3B:
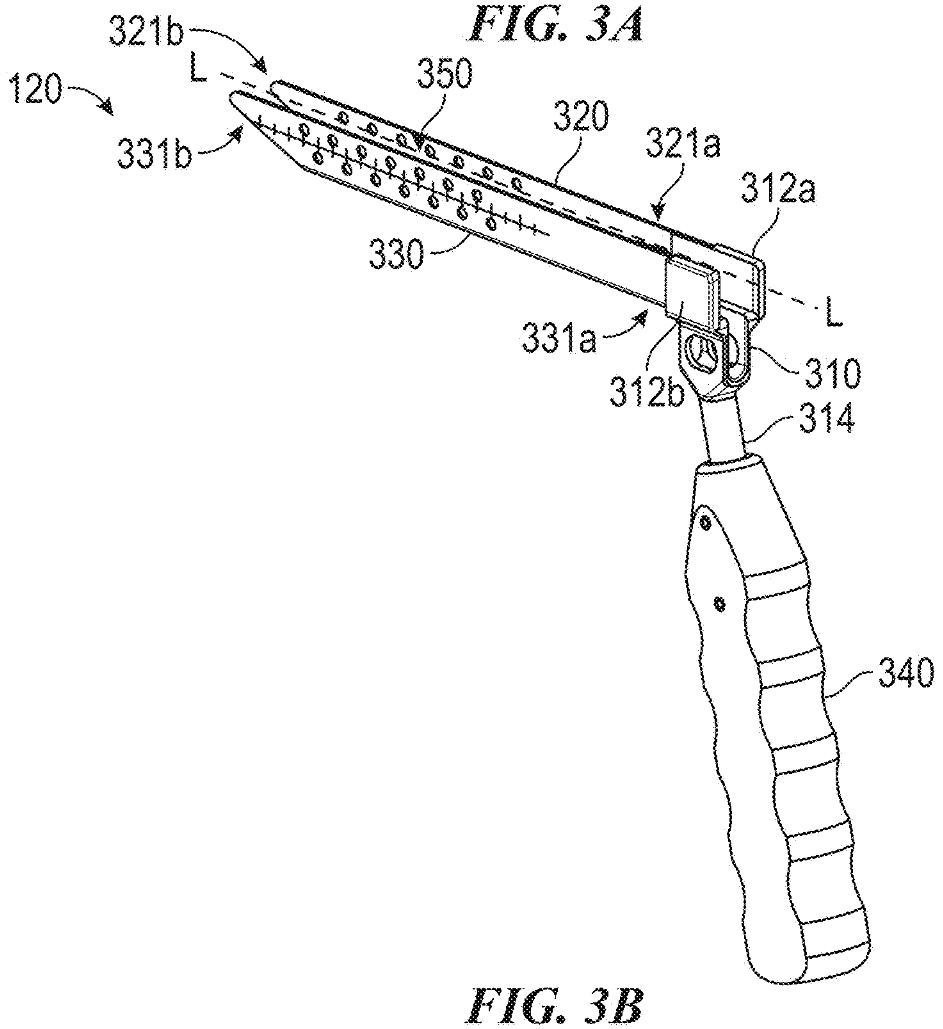
Figure 3C:
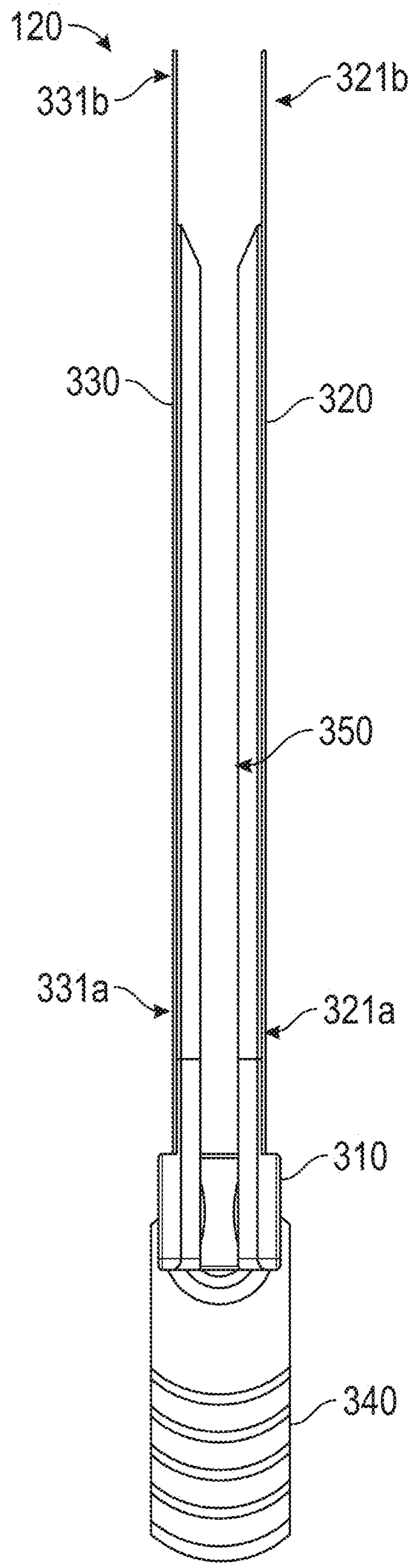
Figure 3D:
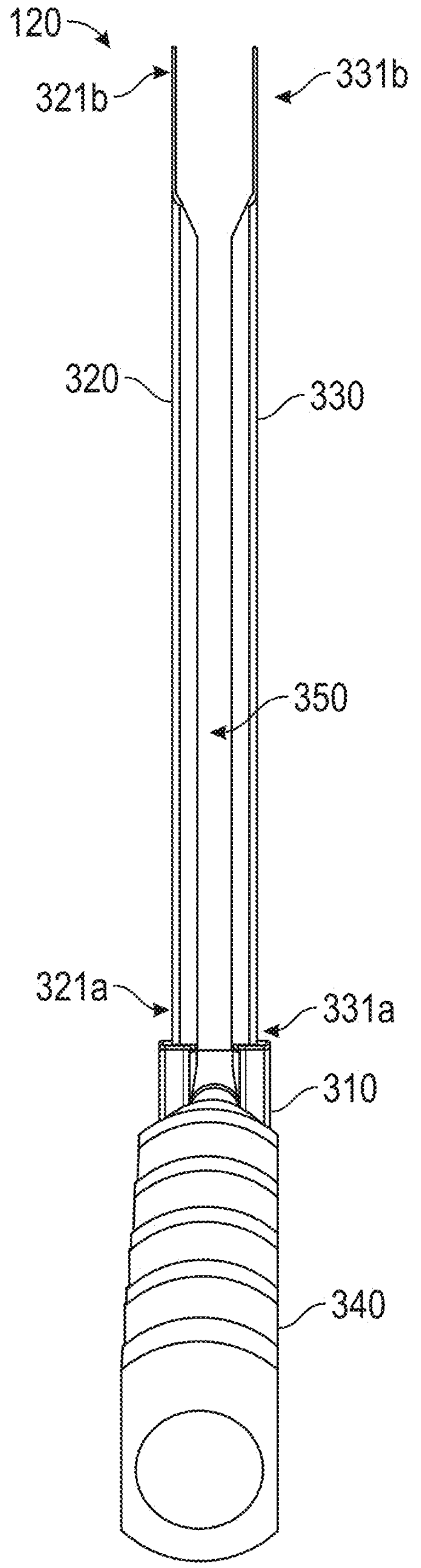

As best shown in FIG. 3B, the elongated split delivery guide 310 can have a generally U-shaped geometry (e.g., cross-section) with a first pushing portion 312*a* and a second pushing portion 312*b*. The first and second insertion members 320, 330 can extend from the first and second pushing portions 312*a*, 312*b*, respectively. The handle assembly 340 can be coupled to a proximal and lower portion 314 of the elongated split delivery guide 310 and can extend at an angle relative to the first and second insertion members 320, 330. As will be described in further detail below, when the device 120 is inserted into a subject, the handle assembly 340 can provide a visual indicator of the orientation of the device 120.

The first insertion member 320 includes a proximal end portion 321*a* that is coupled to the first pushing portion 312*a*, and the second insertion member 330 includes a proximal end portion 331*a* that is coupled to the second pushing portion 312*b*. The first insertion member 320 also includes a distal end portion 321*b* opposite the proximal end portion 321*a*, and the second insertion member 330 includes a distal end portion 331*b* that is opposite the proximal end portion 331*a*. In the illustrated embodiment, the distal end portions 321*b*, 331*b* comprise free, cantilevered, and tapered tips configured to pierce and/or be inserted into a subject. Accordingly, the first and second insertion members 320, 330 can also be referred to herein as a pair of tapered distal sidewalls spaced apart from one another. The first and second insertion members 320, 330 also at least partially define a chamber extending along the longitudinal axis L-L and through which a spinal implant can be delivered, as will be described in further detail below. As an implant is delivered, the first and second insertion members 320, 330 can keep the implant within the channel 350.

Figure 3E:
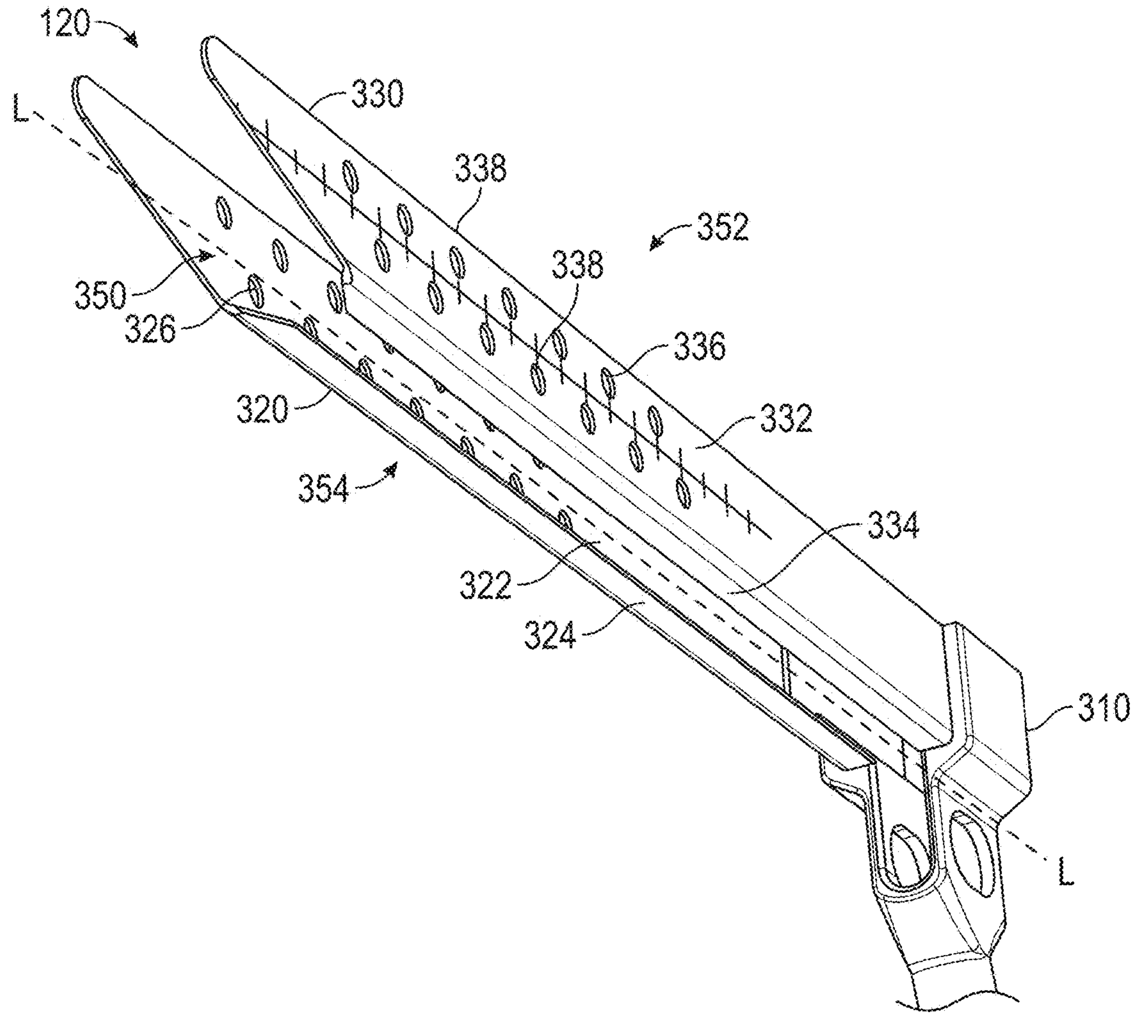
FIGS. 3E and 3F are enlarged bottom isometric and side views, respectively, of portions of the spinal implant delivery device of FIG. 3A.
Figure 3F:
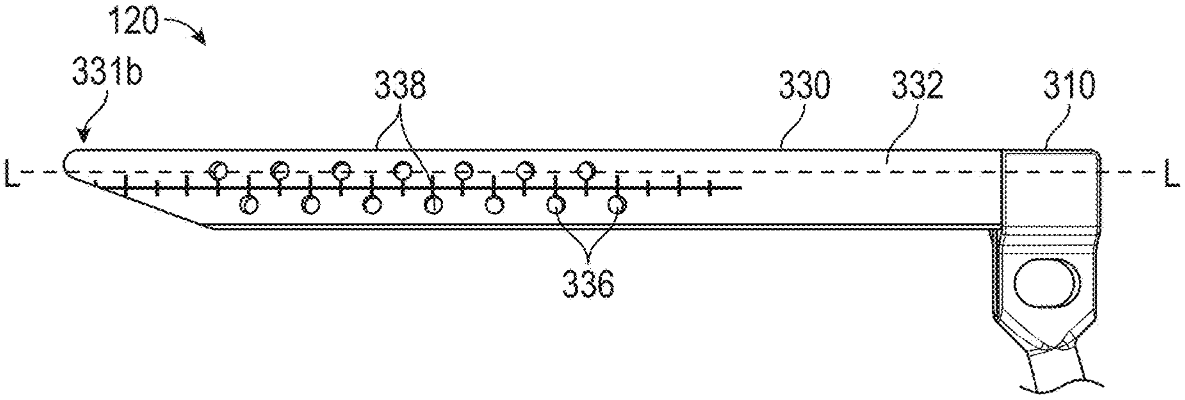

FIGS. 3E and 3F are enlarged bottom isometric and side views, respectively, of portions of the device 120. Referring first the FIG. 3E, the first insertion member 320 includes a first portion 322 (e.g., a first sidewall) and a second portion 324 (e.g., a first bottom) extending substantially perpendicular to the first portion 322. Similarly, the second insertion member 330 includes a third portion 332 (e.g., a second sidewall) and a fourth portion 334 (e.g., a second bottom) extending substantially perpendicular to the third portion 332. The first portion 322 and the third portion 332 can be generally flat and parallel to one another. The second portion 324 and the fourth portion 334 can be generally flat and extend toward one another while defining a longitudinally-extending slot 354 that extends along the longitudinal axis L-L therebetween. In some embodiments, the first and second portions 322, 324 form a first L-shape, and the third and fourth portions 332, 334 form a second L-shape such that the first and second insertion members 320, 330 each comprise elongate structures with an L-shaped cross-section. Thus, a top of the channel 350 has an open side 352 through which an instrument and/or implant can exit, and a bottom of the channel 350 includes the slot 354 that prevents any instrument and/or implant above a predetermined size (based on the gap of the slot 354) from exiting. Accordingly, the elongated split delivery guide 310, as a whole, can have a generally U-shaped cross-section taken perpendicular to the longitudinal axis L-L.

Referring next to FIGS. 3E and 3F together, each of the first and second insertion members 320, 330, and more particularly, the first and third portions 322, 332 can include a first plurality of apertures 326 and a second plurality of apertures 336, respectively. The first and/or third portions 322, 332 can also include distance indicators 338 along the longitudinal axis L-L. In the illustrated embodiment, the distance indicators 338 include marks labeled with specific distance measurements (e.g., in 1 mm, 2 mm, 5 mm, 10 mm, or 15 mm increments from the distal end portion 331*b*). The apertures 336 can be aligned with and/or arranged along the distance indicators 338, as shown.

In operation, the tapered tips of the distal end portions 321*b*, 331*b* can pierce through the subject's skin and/or tissue as the device 120 is inserted into the subject. The distance indicators 338 can visually signal to a surgeon or other user of the device 120 how deep the device 120 has been inserted into the subject. For example, the distance indicator 338 at the subject's skin surface can indicate the total depth that the device 120 has been inserted. In another example, a visualization instrument (e.g., the visualization instrument 140) can be used to determine the position of the device 120 based on the distance indicators 338. As a spinal implant is delivered through the channel 350, the visualization instrument can provide viewing through the apertures 326, 336 to view the position of the implant relative to the device 120. The apertures 326, 336 can be particularly advantageous in embodiments in which the first and second insertion members 320, 330 are made from opaque materials (e.g., metal). However, the apertures 326, 336 can still be particularly in embodiments in which the first and second insertion members 320, 330 are made from transparent or translucent materials (e.g., plastics), such as by providing a clearer through-view of the implant being delivered. Therefore, the apertures 326, 336 and the distance indicators 338 can assist a surgeon or other operator during an implant procedure or other surgical procedure in positioning and/or orienting the device 120 and delivering the implant to the target site with precision.

As mentioned above and discussed in greater detail below, the bottom of the device 120 including the slot 354 can prevent from any instruments and/or implant disposed in the channel 350 from moving or angling out of the channel 350, thereby protecting adjacent tissue and nerves. In the illustrated embodiment, the handle assembly 340 is oriented on the side of the slot 354 and away from the open side 352 (see FIGS. 3A and 3B), allowing a surgeon or other user to conveniently determine which side of the device 120 includes the slot 354 when the device is, for example, inserted in a subject. In other embodiments, the handle assembly 340 can be oriented on the open side 352 and away from the side of the slot 354.

Figure 4:
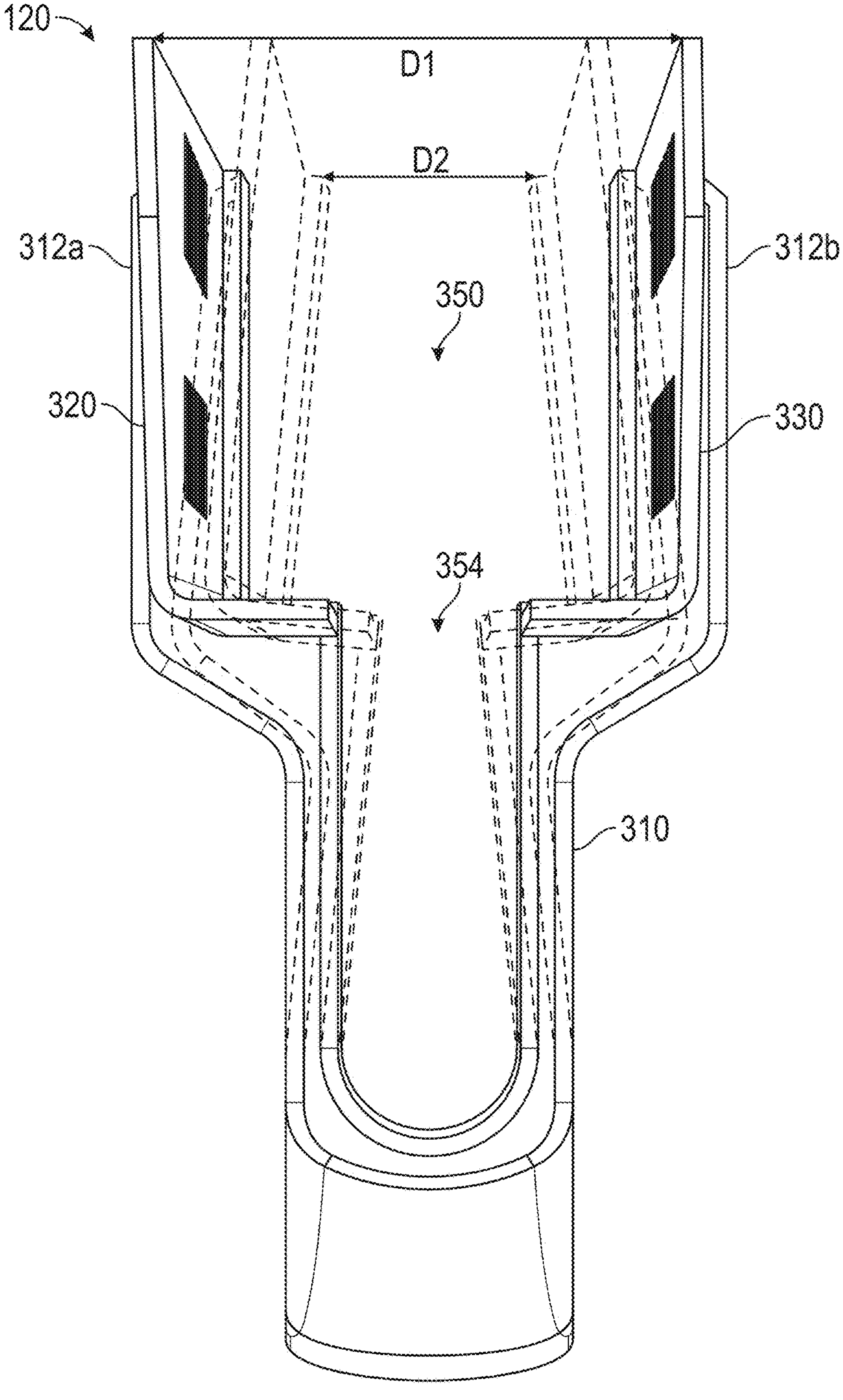
FIG. 4 is a front view of a portion of the spinal implant delivery device of FIG. 3A in an uncompressed state and in a compressed state.

FIG. 4 is a front view of a portion of the device 120 in an uncompressed or neutral state and in a compressed state (in phantom lines). When the device is in the neutral state, the first and third portions 322, 332 of the first and second insertion members 320, 330, respectively, are oriented parallel to one another and are separated by a first distance D1. In some embodiments, the elongated split delivery guide 310 has a stiffness or elasticity that allows the elongated split delivery guide 310 to bias the first and second insertion members 320, 330 to remain separated by the first distance D1. Prior to inserting the device 120 in a subject, the first and second pushing portions 312*a*, 312*b* of the elongated split delivery guide 310 are movable toward one another (e.g., pushed, compressed, or squeezed manually) such that the device 120 is in the compressed state. When in the compressed state, the first and second insertion members 320, 330 are no longer oriented parallel to one another and the top ends of the first and second insertion members 320, 330 are separated by a second distance D2 that is smaller than the first distance D1. The slot 354 can also be narrowed when the device is in the compressed state.

In some embodiments, the device 120 can be inserted into the subject (e.g., advanced towards an implantation site) while in the compressed state such that the profile of the device 120, and thus the area through which the device 120 pierces the subject's tissue, is reduced. When the device 120 (e.g., the distal end portions 321*b*, 331*b*) reaches the target site (e.g., such that a distal portion of the elongated split delivery guide 310 is positioned between vertebral bodies), the first and second pushing portions 312*a*, 312*b* can be released, allowing the elongated split delivery guide 310 to bias the first and second insertion members 320, 330 toward being separated by the first distance D1. When the device 120 returns from the compressed state to the neutral state, such as by releasing the manual squeezing of the first and second pushing portions 312*a*, 312*b*, the first and second insertion members 320, 330 can spread tissue apart or otherwise distract the spine, and the device 120 can create an enlarged space (e.g., an enlarged intervertebral space, a disc space) at the target site. Subsequently, a spinal implant or other device can be passed along the channel 350 and be delivered to the target site.

Figure 5A:
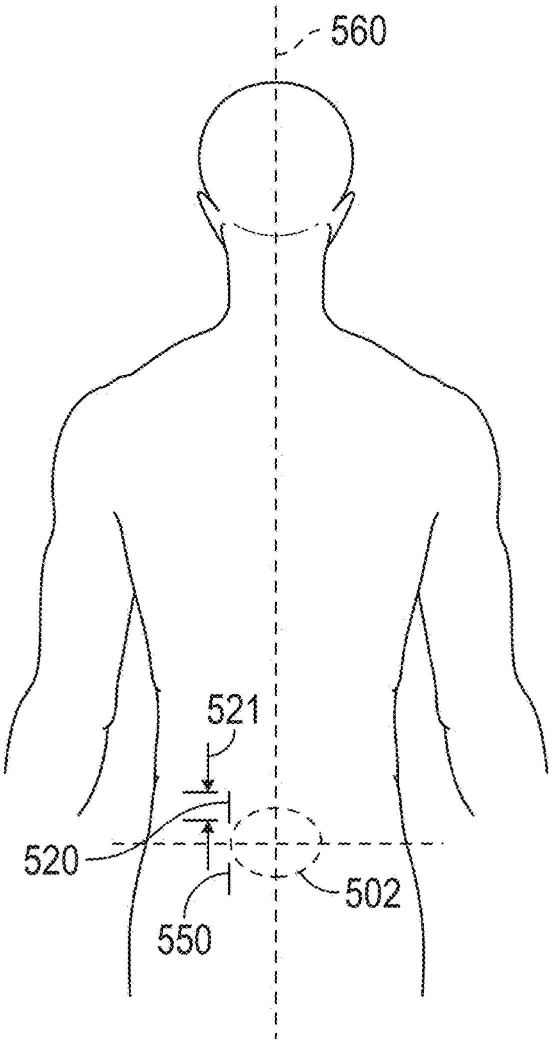
FIGS. 5A and 5B illustrate surgical steps for performing spinal procedures in accordance with embodiments of the disclosure.
Figure 5B:
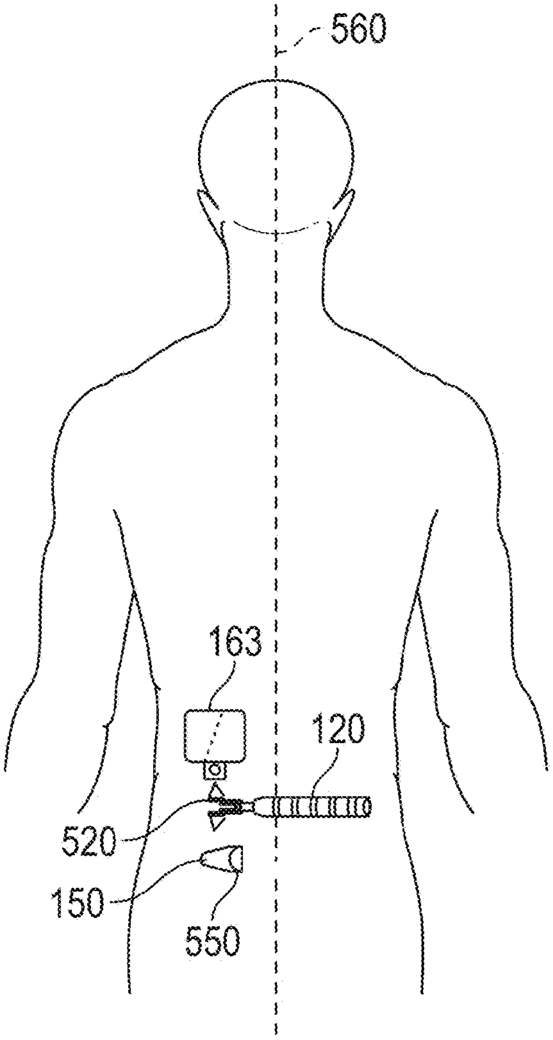

FIGS. 5A and 5B illustrate surgical steps for performing spinal procedures in accordance with embodiments of the disclosure. More specifically, FIG. 5A shows two incisions 520, 550 for accessing the left side of a lumbar spine, and a target site 502 along the subject's midsagittal plane 560. FIG. 5B shows the devices 120, 150 positioned in the incisions 520, 550, respectively. Once the devices 120, 150 are properly inserted, instruments and/or implants (not shown in FIGS. 5A and 5B) can be guided therethrough. The pillow 163 can be positioned adjacent to the devices 120, 150. For example, the illustrated pillow 163 is positioned adjacent to the device 120. The user's left hand can be supported by the pillow 163 while gripping an instrument that is guided through the devices 120, 150 for longer procedures. Additional pillows can be positioned along the patient to provide support when using the instrument.

Figure 6A:
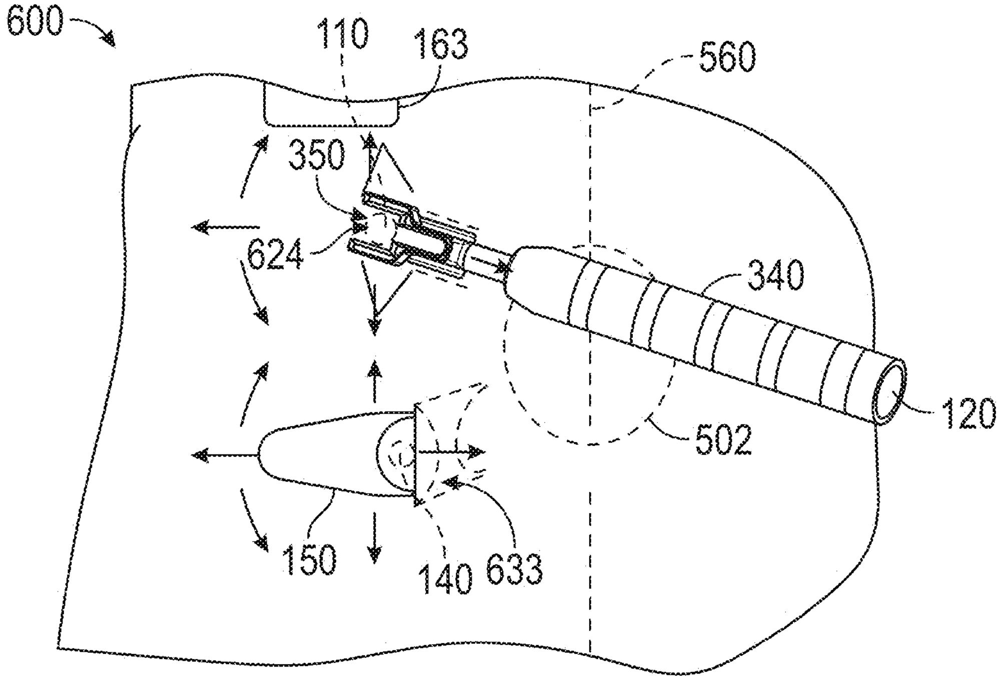
FIGS. 6A and 6B are top views of a spinal surgical system including the spinal implant delivery device of FIG. 3A in different orientations in accordance with embodiments of the disclosure.
Figure 6B:
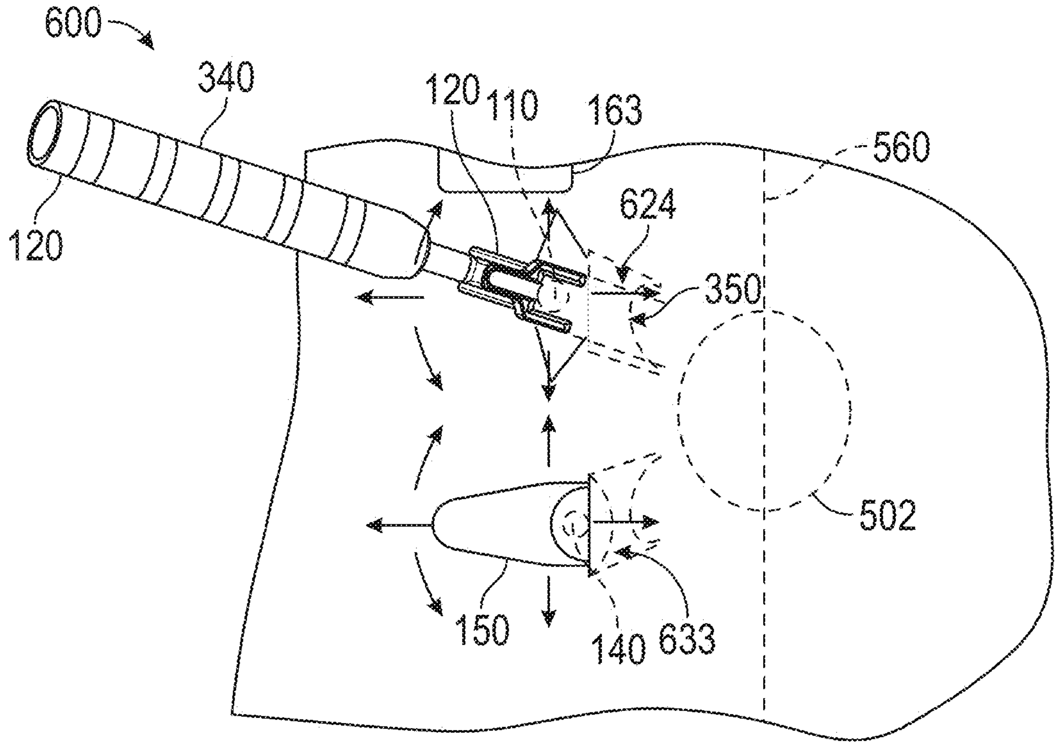

FIGS. 6A and 6B are top views of a spinal surgical system 600 ("the system 600") including the spinal implant delivery device 120 in different orientations in accordance with embodiments of the disclosure. Referring to both FIGS. 6A and 6B, the devices 120, 150 can be angled toward the target site 502 while maintaining a minimum distance of separation. Additional devices can be inserted into the subject to access other regions and/or provide alternative access paths. The instruments 110, 140 (illustrated in dashed line) are positioned in the devices 120, 150, respectively. In particular, the instrument 110 is shown positioned in the channel 350 of the device 150. Tissue 633 extending around the device 150 helps keep portions of the instrument 140 within the proximal ends of the device 150. The devices 120, 150 and the instruments 110, 140 can be moved (e.g., shifted, rotated) together or independently in various directions, as in indicated by arrows. The devices 120, 150 and the instruments 110, 140 can be positioned any number of times. Additionally or alternatively, additional incisions can be made along the patient to reposition the devices 120, 150 or to insert additional cannulas and instruments.

The difference between FIGS. 6A and 6B is the orientation of the device 120. In FIG. 6A, the device 120 is oriented such that the protected side, indicated by the handle assembly 340, faces the target site 502. In FIG. 6B, the device 120 is oriented such that the protected side faces away from the target site 502. On the open side of the device 120, when the instrument or implant 110 is disposed in the channel of the device 120, tissue 624 extending away from the open side of the device 120 helps keep portions of the instrument or implant 110 within the channel of the device 120. On the protected side of the device 120, the barrier formed by the second and fourth portions 324, 334 (FIG. 3E) restrict movement of the instrument or implant 110, thereby protecting adjacent tissue and/or nerves from potential damage.

The decision to orient the device 120 as shown in FIG. 6A or FIG. 6B can be based on multiple factors. For example, depending on the specific position of the target site, the type of surgical procedure involves, and/or the insertion path taken (as discussed above with reference to FIGS. 2A and 2B), a surgeon or other user may decide that either the side facing the target site 502 (as shown in FIG. 6A) or the side facing away from the target site 502 (as shown in FIG. 6B) has tissue and/or nerves that are more susceptible to damage during the procedure compared to the other side. The device 120 can be inserted in the particular orientation that protects the side determined to be more susceptible to damage.

C. SURGICAL TECHNIQUES

Figure 7B:
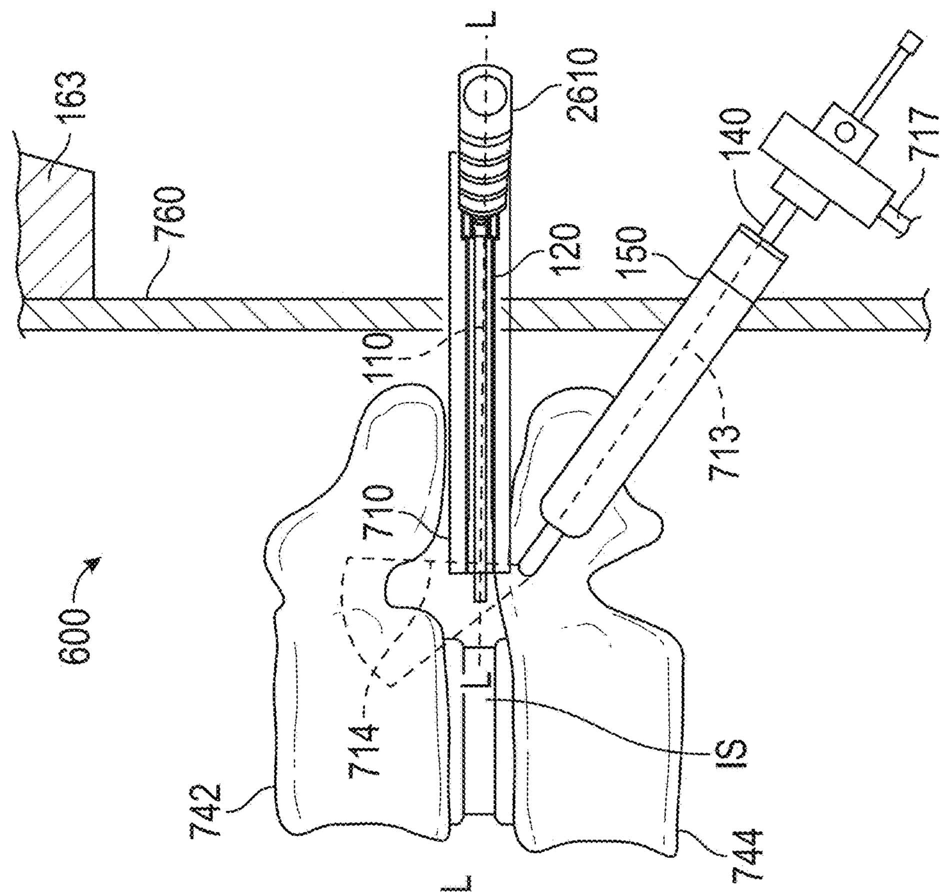
FIGS. 7A and 7B are side views of the spinal surgical system of FIGS. 6A and 6B, respectively.
Figure 7A:
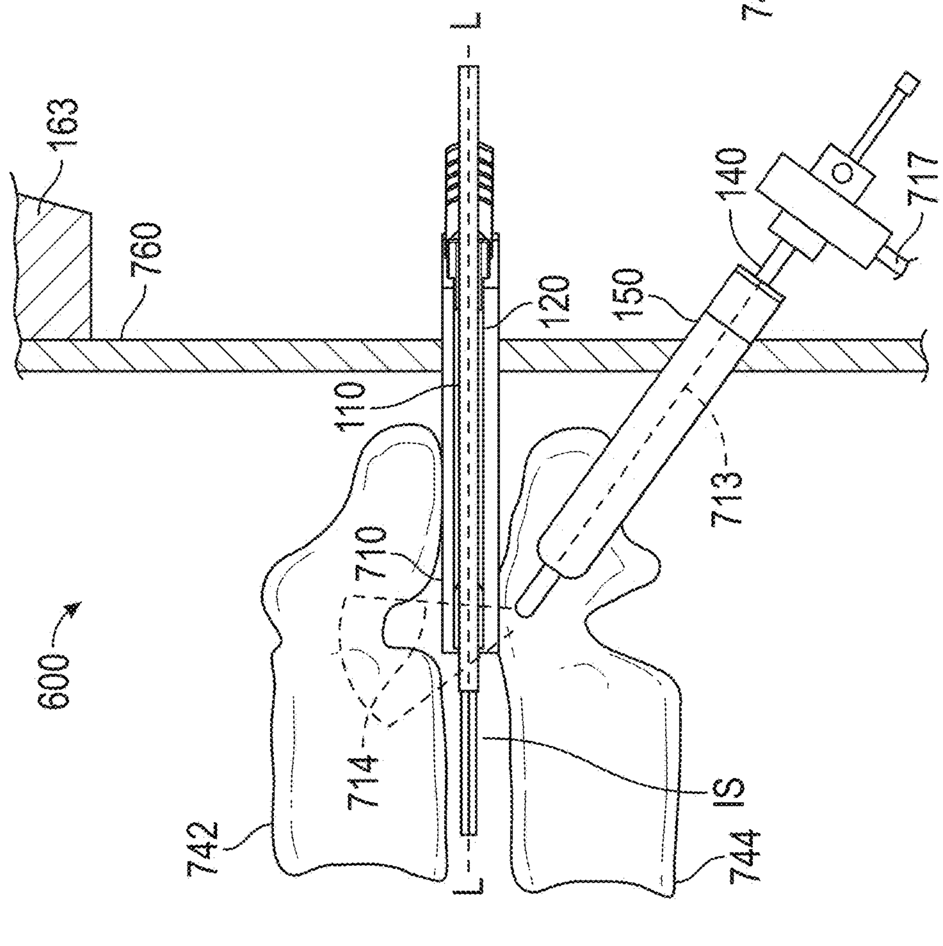
Figure 8A:
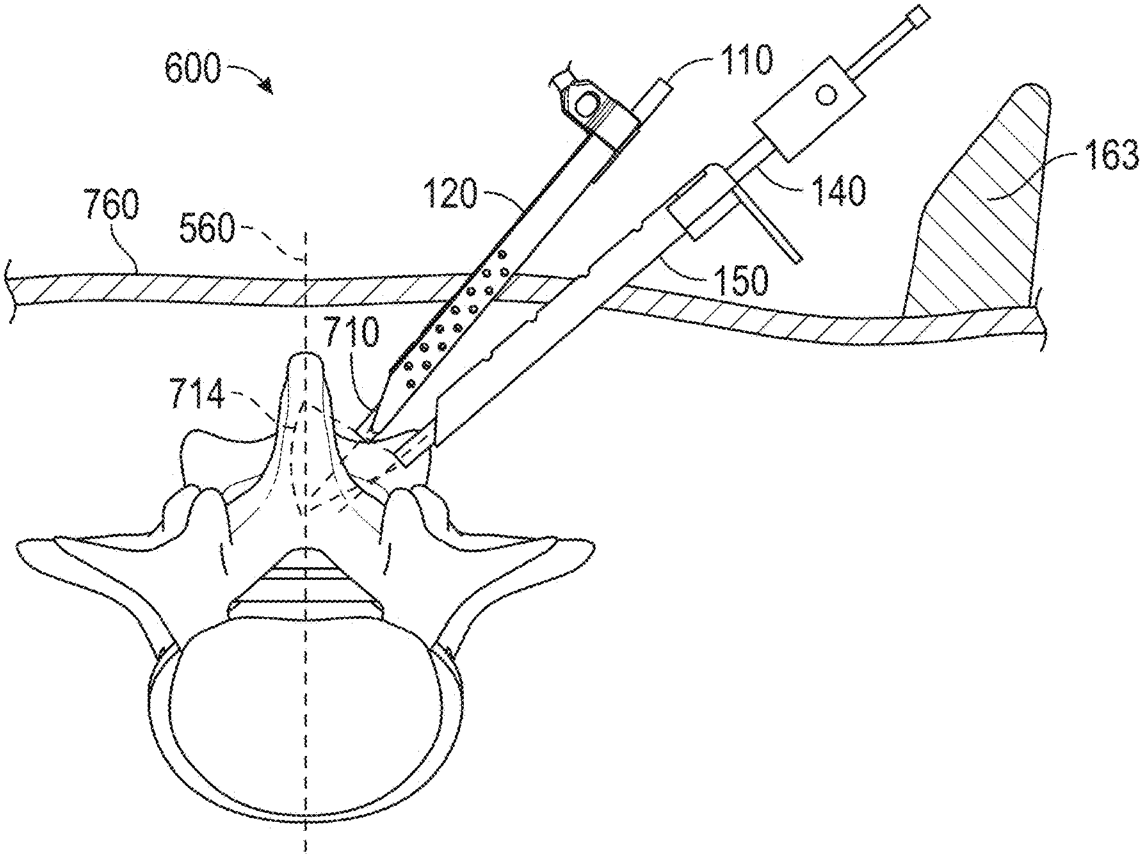
FIGS. 8A and 8B are superior-to-inferior views of the spinal surgical system of FIGS. 6A and 6B, respectively.
Figure 8B:
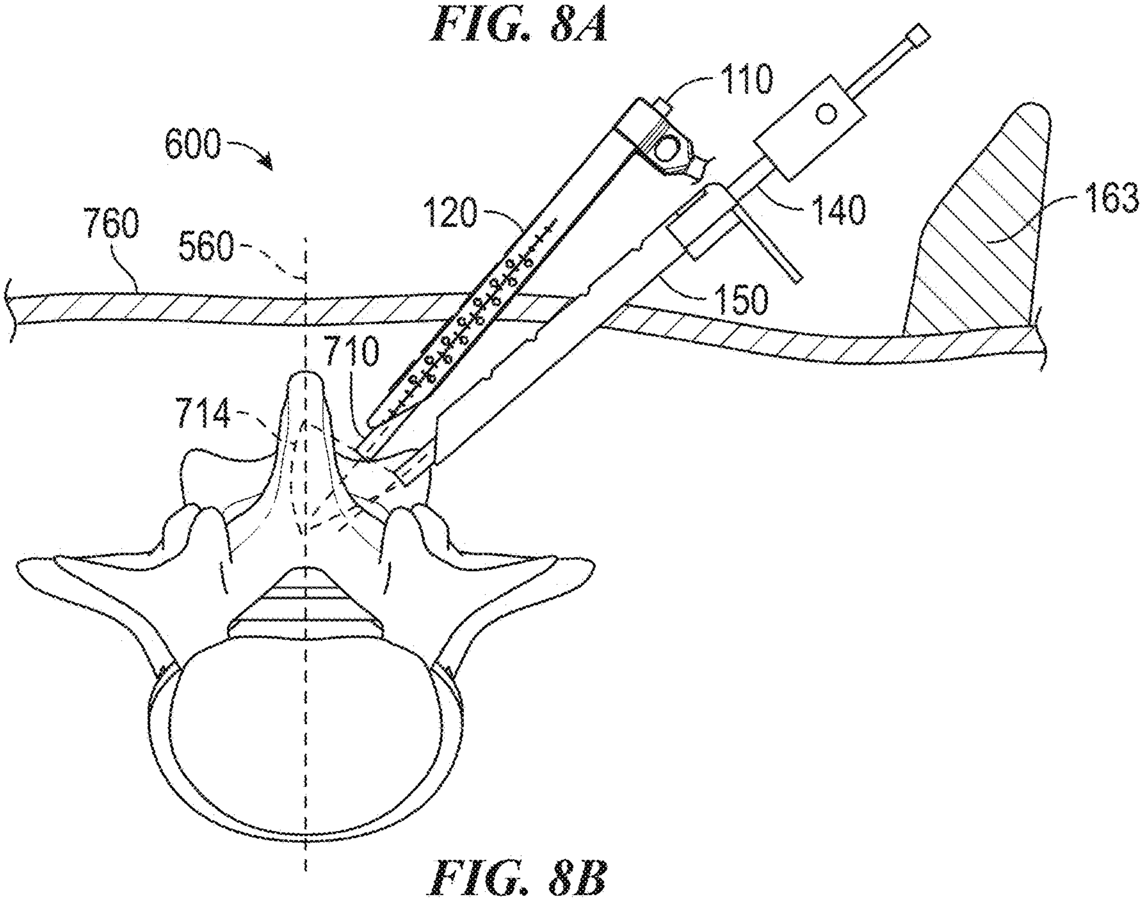

FIGS. 7A and 7B are side views of the spinal surgical system 600. FIGS. 8A and 8B are superior-to-inferior views of the spinal surgical system 600. More specifically, FIGS. 7A and 8A correspond to the orientation of the device 120 illustrated in FIG. 6A, and FIGS. 7B and 8B correspond to the orientation of the device 120 illustrated in FIG. 6B. Referring to FIGS. 7A-8B together, the devices 120, 150 extend through the subject's skin 760 (thickness not illustrated at scale) at different locations and orientations. The visualization instrument 140 has a field of view 714 suitable for viewing the spinal column and can be positioned using, for example, a transforaminal approach, a posterior approach, or a lateral approach. The pillow 163 can be positioned along the patient. An instrument holder 717 (FIGS. 7A and 7B) can hold the visualization instrument 140 at a desired position for visualization and the instrument holder 717 is spaced apart from the pillow 163. In some embodiments, the instrument holder 717 is coupled to the pillow 163.

To allow significant instrument movement, the devices 120, 150 can have axial lengths shorter than a distance from the incision in the skin 760 to the spine. The sizes of the devices 120, 150 can be selected based on the size and configuration of the incision, characteristics of the tissue, the implant to be delivered, etc. For example, the insertion members of the device 120 can be sufficiently long to extend through the subject's skin, fascia, and muscle. The channel of the device 120 can be sufficiently large to allow instruments to be inserted into and distally along the channel, which can prevent or inhibit tearing of tissue. The tissue can cover the open side of the channel to keep the instrument 110 along the device 120, and the protected side can similarly keep the instrument 110 from leaving the channel. Instruments can have relatively small diameters relative to a width of the open side of the device 120 to limit or inhibit tearing of the tissue around the incision. In some procedures, ports can be installed in some incisions and devices can be installed in other incisions without ports. A physician can determine whether to install ports based on the instruments and/or implants to be utilized and the position of the incisions. Devices, ports, and other components can be installed in each of the incisions.

The visualization instrument 140 is positioned outside intervertebral spaces to view at least a portion of an intervertebral space IS, vertebral bodies 742, 744, and/or the distal portion 710 of the instrument 110. Fluoroscopy, MR imaging, CT imaging, direct visualization, or other visualization techniques can be used in addition to or in lieu of the endoscopic viewing. Additional instruments and/or implants can be sequentially delivered through the device 120. In some procedures, multi-modality imaging of the target site can be performed using an external imaging device and the visual visualization instrument 140. The intraoperative imaging can be displayed via one or more digital screens (e.g., endoscopic imaging and fluoroscopy on different screens) in the surgical room.

FIGS. 7A-8B show the devices 120, 150 angled toward the intervertebral space IS to allow the instruments 110, 140 to be kept generally aligned with the respective devices 120, 150. The devices 120, 150 can be manually moved (e.g., shifted, rotated) between different positions and angles while inserted in the subject, as illustrated by the arrows in FIGS. 6A and 6B.

In FIGS. 7A and 8A, the open side of the device 120 faces away from the intervertebral space IS (FIG. 7A) and the subject's midsagittal plane 560 (FIG. 8A) such that the protected side of the device 120 protects the tissue and nerves between the device 120 and the spine. By contrast, in FIGS. 7B and 8B, the open side of the device 120 faces toward from the intervertebral space IS (FIG. 7B) and the subject's midsagittal plane 560 (FIG. 8B) such that the protected side of the device 120 protects the tissue and nerves away from the spine.

In some embodiments, the distal ends of the devices 120, 150 can be moved relative to the spine while the proximal ends of the devices 120, 150 remain generally stationary (e.g., at a fixed axial position relative to the skin 760). Distal portions of the instruments 110, 140 (e.g., the distal portion 710 of the instrument 110) can extend out of the distal ends of the devices 120, 150, respectively, to manipulate the tissue at the target site while shallow tissue (e.g., skin 760) retains the respective devices 120, 150.

Figure 9:
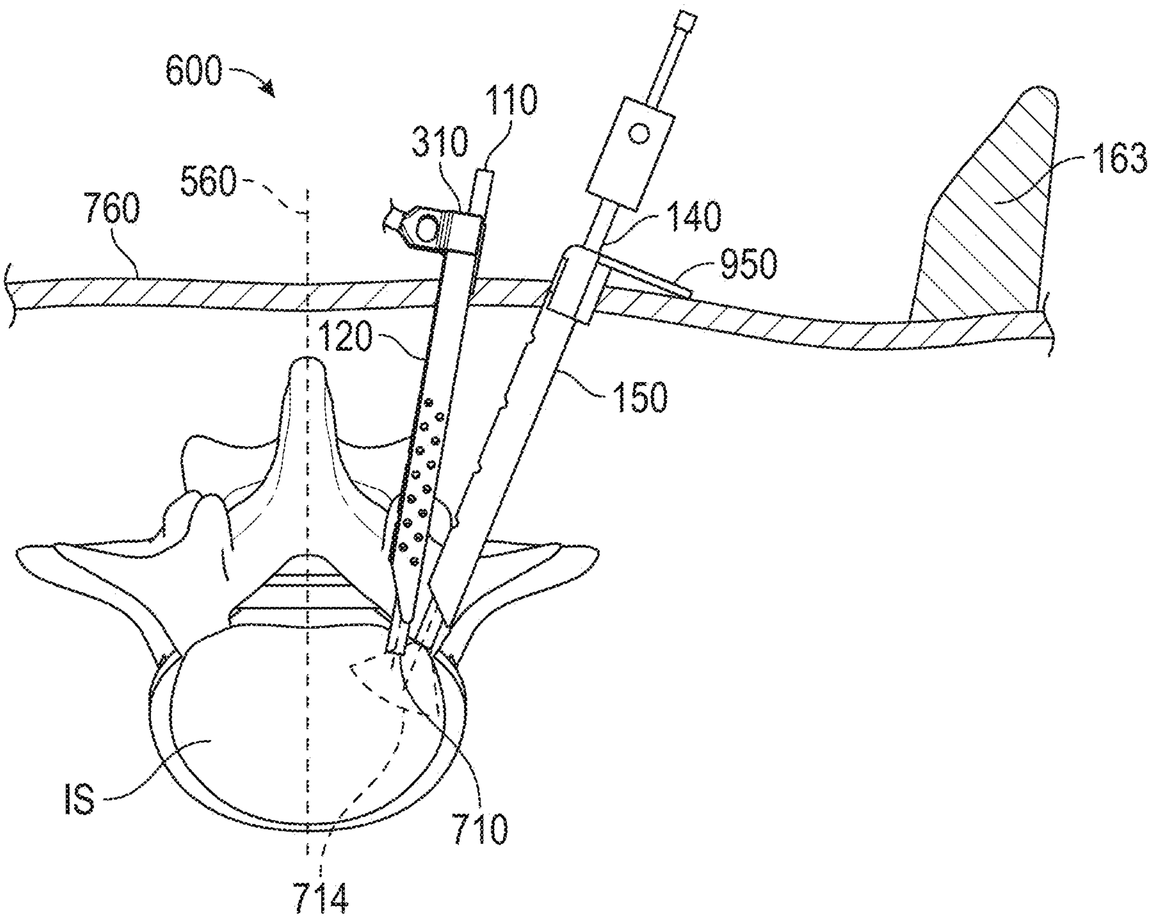
FIG. 9 is another superior-to-inferior view of the spinal surgical system of FIG. 6A.

FIG. 9 is another superior-to-inferior view of the spinal surgical system 600. FIG. 9 is generally similar to FIG. 8A. For example, the devices 120, 150 and the instruments 110, 140 are inserted into the subject. The device 120 can be oriented such that the open side of the device 120 faces generally away from the subject's midsagittal plane 560 and the protected side of the device 120 protects non-targeted tissue (e.g., the tissue and nerves between the device 120 and the center of the spine). However, compared to FIG. 8A, FIG. 9 illustrates the devices 120, 150 and the instruments 110, 140 inserted deeper into the subject. In particular, each of (i) the proximal portion of the elongated split delivery guide 310 and (ii) a flange 950 of the device 150 is positioned to be adjacent to or abut against the skin 760 of the subject. Accordingly, the distal portions of the instruments 110, 140, which extend out of the distal ends of the devices 120, 150, respectively, can reach the intervertebral space IS, as shown, to manipulate the tissue thereat and/or deliver an implant thereto via, e.g., the instrument 110. For example, one or both of the distal ends of the devices 120, 150 can be positioned directly between vertebral endplates (e.g., directly between anterior, lateral, or posterior regions of the vertebral endplates), between facet joints, or the like. The positioning of the distal ends of the devices 120, 150 can be confirmed using, for example, endoscopic imaging, fluoroscopic imaging, x-rays, etc.

Referring to FIGS. 1A-9 together, the lengths of the incisions can be selected to help inhibit or limit axial rotation of the devices 120, 150. A ratio of the length of the incision to an outer width of the devices 120, 150 can be less than or equal to, for example, 1.1, 1.2, 1.3, 1.4, or 1.5. For example, a ratio of a length of the incision to a transverse width of the device 120 can be equal to or less than 1.5 to inhibit or prevent 90 degrees of rotation of the device 120 about its longitudinal axis L-L. This keeps the desired orientation of the device 120 during a procedure. Instrument holders can hold the devices 120, 150, instruments 110, 140, or a combination of devices and instruments. The instrument holders can be particularly useful when performing surgical techniques involving three or more ports.

Instruments can be selected to treat, without limitation, spinal nerve compression (e.g., spinal cord compression, spinal nerve root compression, or the like), spinal disc herniation, osteoporosis, stenosis, or other diseases or conditions. After accessing the work space, the tissue removal tip can remove unwanted tissue, including, without limitation, tissue bulging from discs, bone (e.g., lamina, lateral recesses, facets including the inferior facets, etc.), bone spurs (e.g., bone spurs associated with osteoarthritis), tissue of thickened ligaments, spinal tumors, displaced tissue (e.g., tissue displaced by a spinal injury), or tissue that may cause or contribute to spinal nerve compression. The instrument, as well as other instruments (e.g., rongeurs, debulkers, scrapers, reamers, dilators, etc.), can be used to perform one or more dilation procedures, decompression procedures, discectomies, microdiscectomies, laminotomies, or combinations thereof. In procedures for treating stenosis, the instrument can be used to remove tissue associated with central canal stenosis, lateral recess stenosis, and/or other types of stenosis. In some decompression procedures, the instrument can be a tissue removal device used to, for example, remove bone, separate the ligamentum flavum from one or both vertebrae, cut or debulk the ligamentum flavum, remove loose tissue, and remove at least a portion of the intervertebral disc. Each stage can be performed with a different instrument.

As discussed above, the visualization instrument 140 can be, without limitation, an endoscopic instrument that includes fiber optics suitable to image the treatment site and surrounding tissues, such as the spinal cord, nerves branching from spinal cord, ligaments, vertebrae 742, 744, the intervertebral space IS, or any other features or anatomical structures of interest while an implant is delivered through the device 120. Surrounding non-targeted tissue can be viewed to ensure that the distal tip 710 does not injure it. This allows a physician to remove tissue and/or deliver implants without damaging nerve tissue, the spinal cord, and other non-targeted tissue.

In some embodiments, the visualization instrument 140 can be a steerable to facilitate navigation around anatomical features. The visualization instrument 140 can include a fiber-optic scope or a flexible or rigid instrument with one or more illumination elements (e.g., fiber optics for illumination) or imaging elements (e.g., charge-coupled devices for imaging) suitable for visualizing the interior of otherwise inaccessible sites. In some embodiments, the visualization instrument 140 can be rod-lens endoscopes with an outer diameter equal to or smaller than about 2 mm, 3 mm, 4 mm, 5 mm, 6 mm, 8 mm, or 10 mm, and a length equal to or shorter than about 15 cm, 20 cm, 30 cm, or 40 cm. The visualization instruments 140 can also have integrated irrigation features (e.g., valves, flow control buttons, fluid lumens, return lumens), connectors (e.g., electrical connectors, fluidic connectors, etc.), access ports (e.g., access ports connected to lumens, such as lumens through which instruments can pass), or the like. In embodiments with an angled lens, the visualization instrument can have approximately 0-degree, 10-degree, 15-degree, 30-degree, or 45-degree lens angles, which are toward a light source. In other angled lens embodiments, the visualization instrument can have an approximately 15-degree, 30-degree, or 45-degree lens angled away from a light source. The angle of the lens can be selected based on the area to be viewed. In some posterior or lateral spinal procedures, a 0-degree lens can provide a wide-angle view suitable for viewing nerve roots, the spinal cord, and intervertebral space. A 30- or 45-degree lens endoscope angled toward the light source can be used to provide an angled view toward, for example, the spine or midsagittal plane to view, for example, the spinous processes, spinal cord, or central regions of the intervertebral space. A 30- or 45-degree lens endoscope angled away from the light source can be used to provide an angled view toward the lateral features or the spine, such as nerve roots at the neural foramen, side regions of the intervertebral space, or the like.

D. EXAMPLES

The present technology is illustrated, for example, according to various aspects described below as numbered examples (1, 2, 3, etc.) for convenience. These are provided as examples and do not limit the present technology. It is noted that any of the dependent examples may be combined in any combination, and placed into a respective independent example. The other examples can be presented in a similar manner.

1. A method for delivering a spinal implant to a subject's spine, the method comprising:
   - inserting an implant delivery device in a subject, wherein the implant delivery device includes:
     - a handle assembly; and
     - an elongated split delivery guide coupled to the handle assembly and defining a delivery channel, wherein the elongated split delivery guide includes first and second insertion members defining a longitudinally-extending slot positioned along a bottom of the delivery channel, wherein the first and second insertion members are movable toward each other to narrow the delivery channel for advancing the elongated split delivery guide toward an implantation site in a patient; and
   - delivering a spinal implant to the subject's spine along the delivery channel toward the implantation site while the first and second insertion members keep the implant within the channel.

2. The method of example 1, wherein:
   - the first insertion member extends from the handle assembly and includes a first bottom and a first sidewall extending substantially perpendicular to the first bottom,
   - the second insertion member extends from the handle assembly and spaced apart from the first insertion member, the second insertion member includes a second bottom and a second sidewall extending substantially perpendicular to the second bottom and substantially parallel to the first sidewall, and the first and second bottoms extend toward each other and define the slot.

3. The method of example 1 or example 2, wherein, the elongated split delivery guide is biased to keep the first and second insertion members spaced apart by a first distance, and wherein the method further comprises:

compressing, prior to inserting the device in the subject, the device such that the first and second insertion members are spaced apart by a second distance smaller than the first distance;

releasing, after inserting the device in the subject, the device such that the elongated split delivery guide biases the first and second insertion members toward being spaced apart by the first distance.

4. The method of any one of examples 1-3, wherein:

the first insertion member includes distance indicators and a plurality of apertures arranged along the distance indicators, inserting the device in the subject comprises inserting device by a predetermined distance based on the distance indicators, and delivering the spinal implant comprises determining a position of the spinal implant based on a view of the spinal implant through the plurality of apertures.

5. The method of any one of examples 1-4, further comprising moving the spinal implant along the elongated split delivery guide while a distal portion of the elongated split delivery guide is positioned directly between vertebral bodies of the subject's spine.

6. The method of any one of examples 1-5, further comprising:

positioning a distal portion, in a compressed configuration, of the elongated split delivery guide between vertebral bodies of the subject's spine; and allowing expansion of the distal portion toward an expanded configuration to distract the subject's spine.

7. A method for accessing an intervertebral space of a subject's spine, the method comprising:

inserting a delivery device into a subject, the delivery device including:

a handle assembly, and an elongated split delivery guide coupled to the handle assembly, wherein the elongated split delivery guide includes a first insertion member and a second insertion member each having a sidewall portion and a bottom portion extending from the sidewall portion in a substantially perpendicular direction, wherein each of the first insertion member and the second insertion member is cantilevered and coupled to one another at a proximal portion of the elongated split delivery guide, wherein the sidewall portion of the first insertion member and the sidewall portion of the second insertion member are biased to extend parallel to one another, and wherein the sidewall portions and the bottom portions of the first and second insertion members define a delivery channel of the elongated split delivery guide; and passing a surgical device along the delivery channel of the elongated split delivery guide and toward an intervertebral space of the subject.

8. The method of example 7, wherein the elongated split delivery guide includes (i) a protected face defined by the bottom portions of the first and second insertion members and (ii) an open side opposite the protected face, and wherein inserting the delivery device comprises orienting the delivery device such that the protected face faces the intervertebral space of the subject when the delivery device is inserted in the subject.

9. The method of example 7, wherein the elongated split delivery guide includes (i) a protected face defined by the bottom portions of the first and second insertion members and (ii) an open side opposite the protected face, and wherein inserting the delivery device comprises orienting the delivery device such that the open side faces the intervertebral space of the subject when the delivery device is inserted in the subject.

10. The method of any one of examples 7-9, further comprising:

compressing, prior to inserting the delivery device in the subject, the proximal portion of the elongated split delivery guide such that the first and second insertion members move toward one another, thereby reducing a profile of the elongated split delivery guide, wherein inserting comprises inserting the delivery device into the subject while the delivery device is compressed.

11. The method of example 10, wherein inserting comprises inserting the delivery device between adjacent vertebral endplates of the subject, and wherein the method further comprises:

releasing, after inserting the delivery device in the subject, the proximal portion of the elongated split delivery guide such that the proximal portion becomes uncompressed and the first and second insertion members move away from one another, thereby spreading the adjacent vertebral endplates apart and expanding the profile of the elongated split delivery guide.

12. The method of any one of examples 7-11, further comprising:

inserting a visualization instrument in the subject such that a distal tip of the visualization instrument is positioned adjacent to the first insertion member of the elongated split delivery guide; and visualizing, via the visualization instrument and a plurality of apertures arranged along a length of the first insertion member, the surgical device passing along the delivery channel of the elongated split delivery guide.

13. The method of example 12, further comprising:

determining, via the visualization instrument and a plurality of depth markings arranged along the length of the first insertion member, a position of the surgical device relative to the subject.

14. The method of any one of examples 7-13, wherein inserting the delivery device comprises inserting the delivery device until a distal tip of the elongated split delivery guide is positioned in the intervertebral space of the subject.

15. The method of any one of examples 7-14, wherein inserting the delivery device comprises inserting the delivery device until the proximal portion of the elongated split delivery guide abuts against a skin of the subject.

16. The method of any one of examples 7-15, wherein passing the surgical device comprises passing a spinal implant along the delivery channel of the elongated split delivery guide and to the intervertebral space of the subject.

17. A spinal implant delivery device, the device comprising:

a handle assembly;

a first insertion member extending from the handle assembly in an insertion direction, wherein the first insertion member includes a first portion and a second portion extending substantially perpendicular to the first portion; and a second insertion member extending from the handle assembly in the insertion direction and spaced apart from the first insertion, wherein the second insertion member includes a third portion and a fourth portion extending substantially perpendicular to the third portion, wherein the second and fourth portions extend toward each other, and wherein the first, second, third, and fourth portions at least partially define a channel through which a spinal implant can be delivered to a subject's spine.

18. The device of example 17, wherein the first portion includes distance indicators along the direction and a plurality of apertures arranged along the distance indicators.

19. The device of example 17 or example 18, wherein the first portion is made from a transparent or translucent material, and wherein the first portion includes distance indicators along the insertion direction.

20. The device of any one of examples 17-19, wherein the first and third portions are biased to extend parallel to one another, and wherein the first and second insertion members are configured to be pushed toward one another such that the first and third portions are no longer parallel to one another, thereby reducing a profile of the device.

21. The device of any one of examples 17-20, wherein the second and fourth portions define a protected side extending along lengths of the first and second insertion members, and wherein the handle assembly is oriented on the protected side.

22. The device of any one of examples 17-21, wherein the second and fourth portions are spaced apart to define a gap therebetween.

23. The device of any one of examples 17-22, wherein each of the first and second insertion members is cantilevered.

24. A spinal implant delivery system, comprising:

a handle assembly; and an implant delivery guide coupled to the handle assembly and including:

a slotted channel member having a compressed configuration for insertion into a disc space between vertebral bodies of a patient and an expanded configuration for distracting the vertebral bodies, and an implant delivery channel defined by the slotted channel member and configured to allow an implant to be delivered into the disc space when the slotted channel member is in the expanded configuration.

25. The spinal implant delivery system of example 24, wherein the implant delivery guide has a pair of cantilevered fingers each having a generally L-shaped cross section.

26. The spinal implant delivery system of example 24 or example 25, wherein the implant delivery guide has a longitudinal axis and a U-shaped cross-section taken perpendicular to the longitudinal axis.

27. The spinal implant delivery system of any one of examples 24-26, further comprising an expandable intervertebral implant having a collapsed state for moving along the implant delivery channel and an expanded state for contacting the vertebral bodies, wherein the expandable intervertebral implant expands outwardly past sidewalls of the implant delivery guide when moved from the collapsed state to the expanded state.

28. The spinal implant delivery system of any one of examples 24-27, wherein the implant delivery guide includes first and second cantilevered insertion members each having tapered distal ends configured to lay flat against the vertebral bodies while a slotted region of the slotted channel member faces a midsagittal plane of the patient.

29. The spinal implant delivery system of any one of examples 24-28, wherein the implant delivery guide includes:

a first insertion member extending from the handle assembly in an insertion direction, wherein the first insertion member includes a first portion and a second portion extending substantially perpendicular to the first portion; and a second insertion member extending from the handle assembly in the insertion direction and spaced apart from the first insertion, wherein the second insertion member includes a third portion and a fourth portion extending substantially perpendicular to the third portion, wherein the second and fourth portions extend toward each other, and wherein the first, second, third, and fourth portions at least partially define the implant delivery channel.

30. The spinal implant delivery system of any one of examples 24-29, wherein the slotted channel member includes distance indicators spaced apart along a longitudinal axis of the slotted channel member and a plurality of apertures arranged along the distance indicators.

31. The spinal implant delivery system of any one of examples 24-30, wherein the slotted channel member comprises a transparent or translucent material.

32. The spinal implant delivery system of any one of examples 24-31, wherein the slotted channel member has first and second sidewalls extending parallel to one another when the slotted channel is in the expanded configuration and extending at a non-parallel orientation relative to one another when the slotted channel is in the compressed configuration.

33. The spinal implant delivery system of any one of examples 24-32, wherein the slotted channel member is configured to move spaced apart distal tapered ends of the slotted channel member towards one another when a proximal end of the slotted channel member is compressed.

34. The spinal implant delivery system of any one of examples 24-33, wherein the slotted channel member includes a pair of tapered distal sidewalls spaced apart from one another.

35. The spinal implant delivery system of any one of examples 24-34, wherein the slotted channel member includes first and second insertion members are configured to be pushed toward one another to reduce a width of a slot between the first and second insertion members.

36. The spinal implant delivery system of any one of examples 24-35, wherein the implant delivery guide includes a pair of members at a bottom of the implant delivery channel, wherein the pair of members defines a slot.

E. CONCLUSION

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and/or firmware would be well within the skill of one skilled in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal-bearing medium used to actually carry out the distribution. Examples of a signal-bearing medium include, but are not limited to, the following: a recordable type of medium such as a floppy disk, a hard disk drive, a CD, a DVD, a digital tape, a computer memory, etc.; and a transmission type medium such as a digital and/or an analog communication medium (e.g., a fiber-optic cable, a waveguide, a wired communications link, a wireless communication link, etc.).

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. Features from various systems, methods, and instruments can be combined with features disclosed in U.S. App. No. 63/611,913; U.S. application Ser. No. 15/793,950; U.S. application Ser. No. 17/902,685; U.S. application Ser. No. 18/335,737; U.S. application Ser. No. 18/464,949; U.S. application Ser. No. 18/470,140; U.S. application Ser. No. 18/764,784; U.S. Pat. Nos. 8,632,594; 9,308,099; 9,820,788; 10,105,238; 10,201,431; 10,322,009; 10,898,340; 11,464,648; 11,950,770; PCT App. No. PCT/US20/49982; and PCT App. No. PCT/US22/21193, which are hereby incorporated by reference and made a part of this application. Variations of the implants are contemplated.

Systems, components, and instruments disclosed herein can be disposable or reusable. For example, the ports, instruments, or cannulas can be disposable to prevent cross-contamination. As used herein, the term "disposable" when applied to a system or component (or combination of components), such as an instrument, a tool, or a distal tip or a head, is a broad term and generally means, without limitation, that the system or component in question is used a finite number of times and is then discarded. Some disposable components are used only once and are then discarded. In other embodiments, the components and instruments are non-disposable and can be used any number of times. In some kits, all of the components can be disposable to prevent cross-contamination. In some other kits, components (e.g., all or some of the components) can be reusable.

The term "substantially" as used herein means within 10% of the stated value. For example, a first component that extends "substantially perpendicular" from a second component can be oriented at an angle between 81-99 degrees relative to the second component. Where the context permits, singular or plural terms may also include the plural or singular term, respectively. Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the present technology. Accordingly, the disclosure and associated technology can encompass other embodiments not expressly shown or described herein.

What is claimed is:

1. A method for delivering a spinal implant to a subject's spine, the method comprising:

compressing an implant delivery device, wherein the implant delivery device includes:

a handle assembly; and an elongated split delivery guide coupled to the handle assembly and defining a delivery channel, wherein the elongated split delivery guide includes first and second insertion members defining a longitudinally-extending slot positioned along a bottom of the delivery channel, wherein the first and second insertion members are movable toward each other to narrow the delivery channel for advancing the elongated split delivery guide toward an implantation site in a patient, wherein the elongated split delivery guide is biased to keep the first and second insertion members spaced apart by a first distance, wherein compressing comprises compressing the implant delivery device such that the first and second insertion members are spaced apart by a second distance smaller than the first distance;

inserting, after compressing the device, the implant delivery device in the subject;

releasing, after inserting the device in the subject, the implant delivery device such that the elongated split delivery guide biases the first and second insertion members toward being spaced a rt by the first distance; and delivering a spinal implant to the subject's spine along the delivery channel toward the implantation site while the first and second insertion members keep the spinal implant within the channel.

2. The method of claim 1, wherein:

the first insertion member extends from the handle assembly and includes a first bottom and a first sidewall extending substantially perpendicular to the first bottom, the second insertion member extends from the handle assembly and spaced apart from the first insertion member, the second insertion member includes a second bottom and a second sidewall extending substantially perpendicular to the second bottom and substantially parallel to the first sidewall, and the first and second bottoms extend toward each other and define the slot.

3. The method of claim 1, wherein:

the first insertion member includes distance indicators and a plurality of apertures arranged along the distance indicators, inserting the device in the subject comprises inserting device by a predetermined distance based on the distance indicators, and delivering the spinal implant comprises determining a position of the spinal implant based on a view of the spinal implant through the plurality of apertures.

4. The method of claim 1, further comprising moving the spinal implant along the elongated split delivery guide while a distal portion of the elongated split delivery guide is positioned directly between vertebral bodies of the subject's spine.

5. The method of claim 1, further comprising:

positioning a distal portion, in a compressed configuration, of the elongated split delivery guide between vertebral bodies of the subject's spine; and allowing expansion of the distal portion toward an expanded configuration to distract the subject's spine.

6. A method for accessing an intervertebral space of a subject's spine, the method comprising:

inserting a delivery device into a subject, the delivery device including:

a handle assembly, and an elongated split delivery guide coupled to the handle assembly, wherein the elongated split delivery guide includes a first insertion member and a second insertion member each having a sidewall portion and a bottom portion extending from the sidewall portion in a substantially perpendicular direction, wherein each of the first insertion member and the second insertion member is cantilevered and coupled to one another at a proximal portion of the elongated split delivery guide, wherein the sidewall portion of the first insertion member and the sidewall portion of the second insertion member are biased to extend parallel to one another, and wherein the sidewall portions and the bottom portions of the first and second insertion members define a delivery channel of the elongated split delivery guide;

inserting a visualization instrument in the subject such that a distal tip of the visualization instrument is positioned adjacent to the first insertion member of the elongated split delivery guide;

passing a surgical device along the delivery channel of the elongated split delivery guide and toward an intervertebral space of the subject; and visualizing, via the visualization instrument and a plurality of apertures arranged along a length of the first insertion member, the surgical device passing along the delivery channel of the elongated split delivery guide.

7. The method of claim 6, wherein the elongated split delivery guide includes (i) a protected face defined by the bottom portions of the first and second insertion members and (ii) an open side opposite the protected face, and wherein inserting the delivery device comprises orienting the delivery device such that the protected face faces the intervertebral space of the subject when the delivery device is inserted in the subject.

8. The method of claim 6, wherein the elongated split delivery guide includes (i) a protected face defined by the bottom portions of the first and second insertion members and (ii) an open side opposite the protected face, and wherein inserting the delivery device comprises orienting the delivery device such that the open side faces the intervertebral space of the subject when the delivery device is inserted in the subject.

9. The method of claim 6, further comprising:

compressing, prior to inserting the delivery device in the subject, the proximal portion of the elongated split delivery guide such that the first and second insertion members move toward one another, thereby reducing a profile of the elongated split delivery guide, wherein inserting comprises inserting the delivery device into the subject while the delivery device is compressed.

10. The method of claim 9, wherein inserting comprises inserting the delivery device between adjacent vertebral endplates of the subject, and wherein the method further comprises:

releasing, after inserting the delivery device in the subject, the proximal portion of the elongated split delivery guide such that the proximal portion becomes uncompressed and the first and second insertion members move away from one another, thereby spreading the adjacent vertebral endplates apart and expanding the profile of the elongated split delivery guide.

11. The method of claim 6, further comprising:

determining, via the visualization instrument and a plurality of depth markings arranged along the length of the first insertion member, a position of the surgical device relative to the subject.

12. The method of claim 6, wherein inserting the delivery device comprises inserting the delivery device until a distal tip of the elongated split delivery guide is positioned in the intervertebral space of the subject.

13. The method of claim 6, wherein inserting the delivery device comprises inserting the delivery device until the proximal portion of the elongated split delivery guide abuts against a skin of the subject.

14. The method of claim 6, wherein passing the surgical device comprises passing a spinal implant along the delivery channel of the elongated split delivery guide and to the intervertebral space of the subject.

15. A spinal implant delivery device, the device comprising:

a handle assembly;

a first insertion member extending from the handle assembly in an insertion direction, wherein the first insertion member includes a first portion and a second portion extending substantially perpendicular to the first portion, and wherein the first portion includes distance indicators along the insertion direction and a plurality of apertures arranged along the distance indicators; and a second insertion member extending from the handle assembly in the insertion direction and spaced apart from the first insertion, wherein the second insertion member includes a third portion and a fourth portion extending substantially perpendicular to the third portion, wherein the second and fourth portions extend toward each other, and wherein the first, second, third, and fourth portions at least partially define a channel through which a spinal implant can be delivered to a subject's spine.

16. The spinal implant delivery device of claim 15, wherein the first portion is made from a transparent or translucent material, and wherein the first portion includes distance indicators along the insertion direction.

17. The spinal implant delivery device of claim 15, wherein the first and third portions are biased to extend parallel to one another, and wherein the first and second insertion members are configured to be pushed toward one another such that the first and third portions are no longer parallel to one another, thereby reducing a profile of the device.

18. The spinal implant delivery device of claim 15, wherein the second and fourth portions define a protected side extending along lengths of the first and second insertion members, and wherein the handle assembly is oriented on the protected side.

19. The spinal implant delivery device of claim 15, wherein the second and fourth portions are spaced apart to define a gap therebetween.

20. The spinal implant delivery device of claim 15, wherein each of the first and second insertion members is cantilevered.

21. A spinal implant delivery system, comprising:

a handle assembly; and an implant delivery guide coupled to the handle assembly and including:

a slotted channel member having a compressed configuration for insertion into a disc space between vertebral bodies of a patient and an expanded configuration for distracting the vertebral bodies, wherein the slotted channel member includes distance indicators spaced apart along a longitudinal axis of the slotted channel member and a plurality of apertures arranged along the distance indicators, and an implant delivery channel defined by the slotted channel member and configured to allow an implant to be delivered into the disc space when the slotted channel member is in the expanded configuration.

22. The spinal implant delivery system of claim 21, wherein the implant delivery guide has a pair of cantilevered fingers each having a generally L-shaped cross section.

23. The spinal implant delivery system of claim 21, wherein the implant delivery guide has a longitudinal axis and a U-shaped cross-section taken perpendicular to the longitudinal axis.

24. The spinal implant delivery system of claim 21, further comprising an expandable intervertebral implant having a collapsed state for moving along the implant delivery channel and an expanded state for contacting the vertebral bodies, wherein the expandable intervertebral implant expands outwardly past sidewalls of the implant delivery guide when moved from the collapsed state to the expanded state.

25. The spinal implant delivery system of claim 21, wherein the implant delivery guide includes first and second cantilevered insertion members each having tapered distal ends configured to lay flat against the vertebral bodies while a slotted region of the slotted channel member faces a midsagittal plane of the patient.

26. The spinal implant delivery system of claim 21, wherein the implant delivery guide includes:

a first insertion member extending from the handle assembly in an insertion direction, wherein the first insertion member includes a first portion and a second portion extending substantially perpendicular to the first portion; and a second insertion member extending from the handle assembly in the insertion direction and spaced apart from the first insertion, wherein the second insertion member includes a third portion and a fourth portion extending substantially perpendicular to the third portion, wherein the second and fourth portions extend toward each other, and wherein the first, second, third, and fourth portions at least partially define the implant delivery channel.

27. The spinal implant delivery system of claim 21, wherein the slotted channel member comprises a transparent or translucent material.

28. The spinal implant delivery system of claim 21, wherein the slotted channel member has first and second sidewalls extending parallel to one another when the slotted channel is in the expanded configuration and extending at a non-parallel orientation relative to one another when the slotted channel is in the compressed configuration.

29. The spinal implant delivery system of claim 21, wherein the slotted channel member is configured to move spaced apart distal tapered ends of the slotted channel member towards one another when a proximal end of the slotted channel member is compressed.

30. The spinal implant delivery system of claim 21, wherein the slotted channel member includes a pair of tapered distal sidewalls spaced apart from one another.

31. The spinal implant delivery system of claim 21, wherein the slotted channel member includes first and second insertion members configured to be pushed toward one another to reduce a width of a slot between the first and second insertion members.

32. The spinal implant delivery system of claim 21, wherein the implant delivery guide includes a pair of members at a bottom of the implant delivery channel, wherein the pair of members defines a slot.

* * * * *